United States Patent [19]
Karwoski et al.

[11] Patent Number: 5,397,299
[45] Date of Patent: Mar. 14, 1995

[54] FLUID RECOVERY SYSTEM WITH IMPROVEMENTS MOLDED IN BODY

[75] Inventor: Theodore Karwiski, Hollis; Steve A. Herweck, Nashua; David Cross, Atkinson, all of N.H.

[73] Assignee: Atrium Medical Corporation, Hudson, N.H.

[21] Appl. No.: 817,594

[22] Filed: Jan. 7, 1992

Related U.S. Application Data

[63] Continuation-in-part of Ser. No. 770,614, Oct. 3, 1991, Pat. No. 5,286,282, and a continuation-in-part of Ser. No. 755,032, Sep. 3, 1991, and a continuation-in-part of Ser. No. 647,583, Jan. 28, 1991, Pat. No. 5,154,712, and a continuation-in-part of Ser. No. 556,022, Jul. 20, 1990, Pat. No. 5,114,416.

[51] Int. Cl.⁶ ............................................. A61M 1/00
[52] U.S. Cl. .................................... 604/4; 604/317; 604/321
[58] Field of Search ............... 604/4, 5, 6, 317, 319, 604/320, 321, 118, 119; 137/205

[56] References Cited

U.S. PATENT DOCUMENTS

| | | | |
|---|---|---|---|
| Re. 29,877 | 1/1979 | Kurtz et al. | 128/275 |
| 3,363,626 | 1/1968 | Bidwell et al. | 128/276 |
| 3,363,627 | 1/1968 | Bidwell et al. | 128/276 |
| 4,784,642 | 11/1988 | Everett, Jr. et al. | 604/118 |
| 4,955,873 | 9/1990 | Rajlevsky | 604/322 |
| 4,988,342 | 1/1991 | Herweck et al. | 604/321 |

OTHER PUBLICATIONS

Pleur-evac Instruction Sheet, Undated.

*Primary Examiner*—Sam Rimell
*Attorney, Agent, or Firm*—Lahive & Cockfield

[57] ABSTRACT

A collection vessel for drainage of body fluids includes a molded body with internal dividers constituting ports, baffles and subchambers, and a face plate that closes the body to form a suction-regulated multi-chamber vessel. The vessel has overpressure and underpressure protection, and resists tipping. The molded body includes a wall structure that enhances its utility for blood collection, monitoring, and reinfusion, and incorporates novel valves, ports, handle and stand.

45 Claims, 21 Drawing Sheets

TIME IN SECONDS UNTIL VALVE RELEASES AT -60 $cmH_2O$ VACUUM PRESSURE

FLUID RECOVERY SYSTEM WITH IMPROVEMENTS MOLDED IN BODY

RELATED APPLICATIONS

This application is a continuation-in-part of U.S. patent application entitled Multipurpose Collection Vessel filed by the same inventors as Ser. No. 770,614, filed Oct. 3, 1991, now U.S. Pat. No. 5,286,282, and of Ser. No. 755,032, filed Sep. 3, 1991, and of Ser. No. 647,583, filed Jan. 28, 1991, now U.S. Pat. No. 5,154,712 and of Ser. No. 556,022, filed Jul. 20, 1990, now U.S. Pat. No. 5,114,416 all of which are hereby incorporated by reference.

BACKGROUND OF THE INVENTION

This invention relates to drainage apparatus, and more particularly to apparatus for draining fluids such as blood from a body cavity and for the reuse of such fluids. The invention is especially concerned with such an apparatus that will allow a patient to generate the required vacuum for inspiration but that will automatically protect a patient from being exposed to dangerously high vacuum levels.

Blood recovered from a patient's body cavity (autologous blood) offers significant advantages over blood from other humans (homologous blood). Autologous blood reduces the risk of adverse reactions and transmission of infectious disease, has near normal oxygen carrying capacity and pH, conserves blood supplies, provides a readily available source of compatible blood; and provides cost savings. For these reasons, the practice of reinfusing autologous blood, known as autotransfusion, is expanding rapidly.

Autotransfusion may be used in the emergency room setting to recover blood lost through chest trauma; in the operating room setting to recover blood shed during surgery; or in the intensive care setting to recover shed mediastinal blood following cardiac or other surgery.

Various devices have been developed to drain and collect fluids such as blood from a body cavity for subsequent auto-infusion. The following U.S. patents illustrate prior art developments in drainage and/or auto-infusion devices.

U.S. Pat. Nos. 3,559,647 Bidwell et al
3,683,913 Kurtz et al
3,853,128 Kurtz et al
4,018,224 Kurtz et al
4,112,948 Kurtz et al
4,443,220 Hauer et al
4,540,413 Russo
4,605,400 Kurtz et al In U.S. Pat. No. 3,853,128, for example, there is disclosed a drain apparatus of one piece unitary construction. The device includes a collection chamber for collecting fluids from a body cavity, a water seal chamber for preventing passage of air from the atmosphere into the body cavity, and a manometer chamber for regulating the degree of vacuum in the system. The collection chamber is connected by a thoracotomy tube to the patient's pleural cavity. The device is connected to a suction pump and the amount of liquid in the manometer chamber determines the degree of vacuum imposed. A valve mechanism is provided in the water seal chamber to permit the outflow of gases from the apparatus in the event of a sudden increase in pressure in the device, such as may occur when the patient coughs.

For many years the prior art devices made no provision for autoinfusing simultaneously with draining. A device that allows autotransfusion simultaneously with draining has significant advantages over prior art devices, especially in the emergency room and operating room settings. Elimination of time-consuming intervening steps between collection, transfer of blood, and autotransfusion streamlines the autotransfusion tasks of medical personnel and enhances the utility of autotransfusion.

The prior art drainage devices generally cannot be used to simultaneously collect blood from the pleural cavity and autotransfuse, because there is no provision in prior art devices for automatic regulation of negative pressure during autotransfusion. During autotransfusion, as fluid exits the collection chamber, remaining fluid volume drops and pressure negativity increases. It is important to maintain pressure negativity within a relatively narrow range to keep bleeding to a minimum and to prevent damage to intrathoracic tissue. It is also important to maintain pressure negativity within a relatively narrow range in order to prevent water from being siphoned out of the water seal chamber and into the collection chamber. Loss of water in this manner would render the water seal useless as a one way valve for air.

One approach to the solution to this problem is to provide a chamber comprising a collapsible bag whose volume can change as required. See U.S. Pat. No. 4,443,220. Such blood bags may be removed from the drainage device when full and placed on a stand to effect reinfusion, but these devices are incapable of simultaneous drainage and reinfusion. Another approach is to provide a mechanical pressure regulating mechanism in communication with a collection chamber which functions to regulate the subatmospheric pressure in the collection chamber independent of the chamber's effective volume. See U.S. Pat. No. 4,548,413. However, mechanical pressure regulating mechanisms are costly and often unreliable.

The relative underpressures suitable for drainage of the thoracic cavity are in the range of several centimeters of water, representing a pressure difference of well under 0.01 atmospheres. However, the drainage tube from a patient may itself have a significant volume; as a result, the process of "stripping" the tube to clear its lumen by forcing blockages along the tube may introduce substantial fluctuation in pressure into the drainage vessel. Further, the placing of a separate collection vessel in the suction drainage system alters system volume. For these reasons, the combination of multi-chamber drainage devices with a separate fluid collection chamber for collecting a portion of fluid for reinfusion cannot be expected to maintain a uniform suction at the desired low level. Moreover, such systems for fluid collection are not well adapted for simultaneously both draining fluids and transferring the desired fluids into the circulatory system.

While it is necessary to allow the patient to draw as much vacuum pressure as is required during normal and deep inspiration without breaking the water seal, currently available fluid recovery systems allow dangerously high levels of vacuum to accumulate within the patient's chest. This is due to the ratio of water volume at the bottom of the water seal and the valve design at the top of this chamber. In recognizing this extremely dangerous situation designers have added a manual mechanical push button type valve to the chest drain in order to release accumulated vacuum pressure. Known chest drain systems, therefore, use float valves to maintain high vacuum in the collection chamber and manually operated vents to release high vacuum. There are, however, problems associated with known manual vents.

One problem associated with manual venting of high accumulated vacuum is that because of restrictions in the height of the calibrated water seal column, the operator of the manual vent has no idea how high the vacuum pressure actually is. Additionally the operator will have to visually observe the water seal float valve position and water level, that is the amount of water on top of the valve, and guess at whether or not excess vacuum is present in the system. Then, only if it is known that the patient's chest tubes have been recently stripped or milked, will the operator assume that there is a dangerous level of vacuum. These known manual venting systems do not give any inherent indication that high vacuum is present other than that of the presence of water on top of the float valve.

Another problem with manual venting of excess vacuum is that to alleviate this vacuum the operator must push down on the manual push button atmospheric valve to allow atmospheric pressure to relieve the closed system vacuum. Such a procedure can take the operator anywhere from 30–60 seconds and requires that constant pressure be kept on the manual vent valve. Additionally, the operator must carefully observe and coordinate the level of the water seal with the release of pressure on the manual valve. If the operator does not carefully observe and coordinate the release of pressure on the manual vent, the patient's intrathoracic vacuum could be lowered to a dangerously low level such as atmospheric pressure. Since the purpose of any water seal chest drain system is to restore and maintain a minimum level of vacuum to the patient's chest following surgery, failure to stop manual venting at the proper moment, will cause serious clinical event known as pneumothorax. Such an event will require immediate physician attention.

More recently, multi-chamber drains have been developed which incorporate structures for maintaining suitable levels of suction under a broad range of operating conditions while assuring a high level of cleanliness of the collected blood. Such systems are described, for example, in U.S. Pat. No. 4,988,342.

In so called "wet" drains of the type described in that patent, manufacturing has typically been carried out by molding of an open multi-channel body, and sealing the body with a face plate to define a closed housing having the different manometer, water seal and collection chambers corresponding to subdivisions therein. Over the last several years, a rapidly evolving range of baffles, channels and relief valves have appeared in the body portion of such multi-chamber drains to regulate or affect noise levels, suction uniformity, fluid or suction level display visibility, overpressure spikes and other conditions, and this type of multichamber vessel has become an indispensable adjunct of cardiac and thoracic surgery.

However, for a device which can critically affect operating room activity and also patient safety, further improvements in safety, convenience or effectiveness of operation are always desirable. These multi-chamber vessels are essentially broad shallow box-like containers, stood or hung vertically, through which a voluminous and continual draw of air is maintained bubbling through a small volume of water. Such a structure presents numerous difficulties in maintaining the columns of fluid separate and intact during operation, handling and ultimate disposal.

It is, therefore, an object of the present invention to provide a fluid collection system having improved construction.

It is also an object of the invention to provide a reliable, easily used, inexpensive, and disposable drainage device which bidirectionally modulates pressure during drainage or auto-infusion while minimizing introduction of ambient air to the collected fluids.

It is yet another object of the present invention to provide a versatile device which functions effectively intra-operatively as a suction powered drainage device, as well as post-operatively as a device for draining the pleural and mediastinal cavities while providing improved handling and disposal characteristics.

SUMMARY OF THE INVENTION

The present invention provides a disposable unitary structure for sterile collection of fluids, e.g., blood, from a patient, and in some embodiments for reinfusion of such fluids back to the circulatory system of the patient. The apparatus comprises a rigid collection chamber for receiving fluids from a wound or surgical opening such as in the pleural cavity, a U-shaped water seal chamber for preventing unhindered passage of air from the atmosphere back into the cavity, and generally a manometer chamber for maintaining a selected subatmospheric pressure range in the collection chamber. The collection chamber has at least two ports: the first port is adapted for connection to a tube for drawing fluids from the pleural cavity, wound or opening into the collection chamber; the second port communicates with the water seal chamber. Optionally a third port, controlled by a valve, seal, clamp or diaphragm is adapted for connection with an infusion pump or separate reinfusion or transfer vessel for delivering fluids collected in the collection chamber into the circulatory system of the patient.

The various means for maintaining an underpressure condition, such as the water seal and manometer, are each configured to have a relatively broad and continuous response to pressure fluctuations. The device is thereby operable to maintain a selected subatmospheric pressure range in the collection chamber during outflow of collected fluid, and to permit reinfusion of fluids from the collection chamber simultaneously with drainage from the pleural or other body cavity into the collection chamber. Among the discrete pressure-modulating mechanisms are preferably included a positive-pressure relief valve, an excess negativity relief valve, and also a timed-release float valve, the latter being interposed between one arm of the water seal chamber and the collection chamber.

Such a timed-release float valve is described in applicant's aforesaid U.S. patent application Ser. No. 556,022 filed Jul. 20, 1990.

The device includes means located in the water seal chamber for admitting air into the collection chamber when collection chamber pressure drops below a selected subatmospheric level. The various means for maintaining an underpressure condition, such as the water seal and manometer, are each configured to have both a stable, and a relatively broad and continuous, response to pressure fluctuations. The device is thereby operable to maintain a selected subatmospheric pressure range in the collection chamber during extended periods of inflow or outflow of collected fluid, and to permit reinfusion of fluids from the collection chamber simultaneously with drainage from the pleural or other body cavity into the collection chamber. A structure also prevents water siphoning into the collection chamber as pressure therein decreases, and a novel set of baffles prevents water entrained in air bubbles passing through the water seal from entering the collection chamber.

In addition to the above broad structural features, the improved vessel in one aspect comprises a molded body having outer walls and an open side, plural internal dividers, and a face plate which closes the open side whereby the dividers separate the molded body into plural distinct subchambers for holding fluid, and wherein the molded body includes a passageway between interior and exterior of the vessel, the passageway opening toward the face plate to receive a valve element therein. Assembly of the face plate onto the molded body secures the valve element in position for regulating pressure in the subchambers. Both positive- and negative- pressure relief valve assemblies are accommodated in this way, the manufacture of each valve resulting in fewer assembly steps, reduced component count, and elimination of gluing or other secondary assembly operations.

In another aspect, the improved vessel comprises a body having a back interior surface and plural dividers extending from the back interior surface to channel fluid communication within the body, a face plate closing the body along outer edges thereof such that at least some of the dividers contact the face plate to define separate intercommunicating subchambers of a multichamber collection vessel formed by said body and face plate, wherein one subchamber extends laterally from one side of the vessel and is positioned below an inlet to form a collection chamber for receiving body fluids drawn to said inlet by suction applied to said one subchamber.

In accordance with one feature of this aspect of the invention, the molded body includes a knockout formed adjacent an upper side portion of said subchamber for decanting collected fluid after use. The vessel preferably includes a boss extending outwardly at the upper side portion constituting a thumbgrip leverage point for manually pressing out the knockout. The knockout is formed by thinning an annulus such that a central portion thereof breaks entirely off and falls within said subchamber when pressed.

In accordance with another feature of this aspect of the invention, the collection chamber has a volume and an aspect ratio defined by the interior walls. A mold for forming the body had a central movable mold block assembly which allows forming the chamber walls in different configurations to achieve a high resolution display of fluid collection, or to achieve a high container volume.

In accordance with yet another aspect of the present invention, a multi-chamber drain vessel for the collection of body fluids from a patient by aspiration, comprises plural walls defining a multichamber container having intercommunicating subchambers defining a series of enclosed volumes for constituting a fluid collection chamber, for regulating suction in the collection chamber while sealing the chamber from contamination by the surrounding atmosphere, and includes a stand or other means for holding the vessel in a vertical orientation such that body fluids enter the vessel through a collection tube attached at the top of the vessel and flow downwardly to pool in the collection chamber, and further includes a self-sealing injection port positioned in a horizontally extending wall of the vessel above the collection chamber, where liquids are conveniently injected into the collected fluid with one hand without tipping the vessel.

In accordance with yet another aspect of the invention, a multi-chamber drain vessel for aspirating and collecting fluid from a patient includes a molded body defining a plurality of vertically disposed adjacent intercommunicating chambers closed by a common face plate, the chambers including a U-shaped manometer column, a U-shaped water seal column and a fluids collection chamber, the U-shaped manometer column having on its downstream side a large arm portion connected to a suction source and through which air bubbles to maintain a set maximum level of suction, and the U-shaped water seal column having a large arm communicating at its top with the suction source and a small arm communicating at its top with the fluids collection chamber, the large and small arms of the water seal column joining in a sealing pool at their bottom ends which receives fluid to form an air barrier when said drain is oriented in an upright position for operation with both said arms extending vertically, the drain further having a supporting base for supporting the drain in a free-standing upright position whereby it is occasionally knocked onto its back such that the face plate faces upwardly and the large arm slopes downwardly from said sealing pool toward the top of the large arm.

According to this aspect, the bottom end of the large arm includes a pool chamber having a ceiling that extends forward toward the face plate to meet the upper portion of said large arm, thus forming a broad deep trap chamber, in both the upright and horizontal positions, for preventing, when the drain is knocked over on its back, fluid from passing into the upper portion of the large arm. A portion of the manometer chamber large arm includes a side chamber separated by a baffle, which extends laterally occupying space above the pool chamber when the drain vessel is upright for containing a volume of suction control fluid in the manometer column large arm through which no air bubbles. The side chamber and pool chamber of the respective manometer and seal columns occupy the same columnar space of the drain, thereby simultaneously reducing fluid loss or spillage, and enhancing stability of fluid levels in both the water seal and the manometer columns while preserving the essential compactness of the device. Above the seal chamber the large arm is both broad and recessed, when viewed from the rear of the drain vessel, thus providing a protective space. Advantageously, fragile accessories are fitted into this recess when the vessel is packaged and shipped, so they are not damaged prior to set-up.

According to another aspect of the invention the vessel includes a collection chamber that is split into first and second subchambers by a divider wall. Both subchambers receive the common regulated suction, and respective first and second inlets are located above the subchambers, with a filter further interposed between the first inlet and the first subchamber, which also has an outlet port. The first subchamber functions as an autotransfusion (ATS) chamber, while the second subchamber operates as a general purpose or cardiotomy collection vessel, distinct from the ATS supply.

Preferably the divider wall follows an angled contour to provide one or more sequential portions of the first subchamber that have a low volume-to-linear wall dimension ratio. This allows resolution of subchamber volume at a level appropriate for pediatric blood collection, bleed rate evaluation, and autoinfusion monitoring.

According to still another aspect of the invention, a collection chamber has a graphic mask through which the level of collected fluid is observed. A sloping floor causes the fluid level to progress along an oblique line at a greater rate than the vertical rise of fluid. A block graphic pattern in the graphic mask forms a readily perceived discontinuity with the fluid surface, allowing the collected volume to be read from a graduation scale with excellent clarity and enhanced accuracy. The sloping floor may funnel fluid into a narrow side column, effectively doubling the volume that can be displayed with high resolution.

BRIEF DESCRIPTION OF THE DRAWING

For a fuller understanding of the nature and objects of the invention, reference should be made to the following detailed description and the accompanying drawings, in which

FIG. 4c is a cross-sectional view of the float valve of FIG. 1, the view being oriented to that of FIG. 4a;

Throughout the description, like reference characters in respective drawn figures indicate corresponding parts.

DESCRIPTION OF ILLUSTRATED EMBODIMENTS

Figure 1:
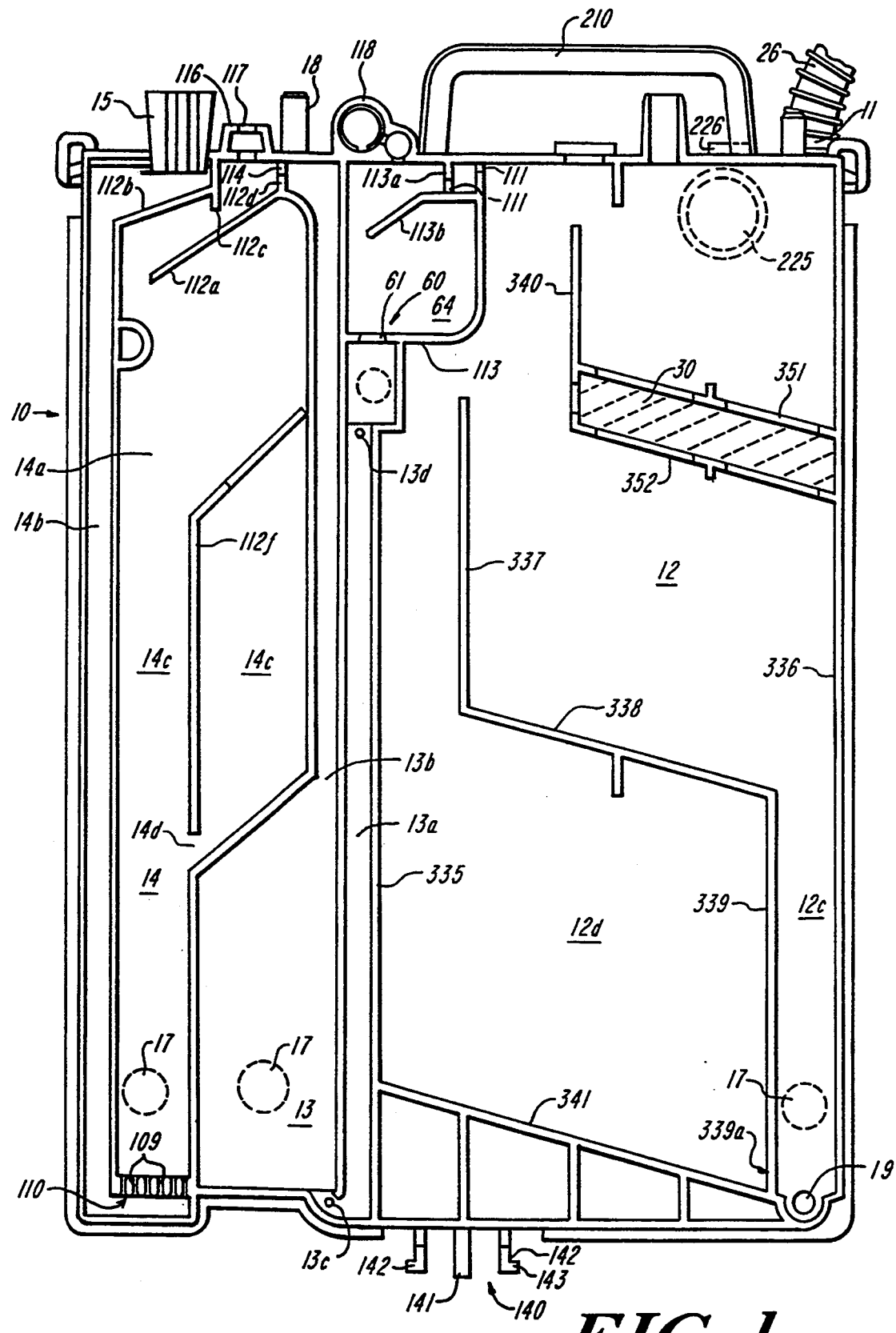
FIG. 1 is a front elevation of the body portion of a drain device according to the invention.

Referring to FIG. 1, there is shown the body 10 of a chest drain device which is preferably of unitary construction, fabricated by adhering together rigid molded parts of plastic, at least some of which, as described in further detail below, are transparent. The device generally comprises a collection chamber 12, a U-shaped water seal chamber 13, and a suction control or manometer chamber 14.

Blood and other fluids from a patient's body cavity enter drain device 10 through a tube 26 attached to inlet port 11, and are collected in collection chamber 12 after passing through a gross filter 30 which traps macroscopic debris such as blood clots, bone fragments, and the like entrained in the incoming fluid. Filter 30 preferably has an approximate pore size of 80–270 microns, suitable for filtration of such contaminants as bone and other tissue not suitable for blood transfusion. Collection chamber 12 is preferably provided with graduated markings which appear on a face plate that closes the body, as described below, indicating the volume of fluid it contains.

Water seal chamber 13 provides a barrier to reflux of atmospheric air into a patient's pleural cavity. Water seal chamber 13 is a U-shaped chamber having two arms 13a and 13b, and preferably is provided with a septum or grommet 17 for filling or replenishing water via a syringe needle. Water seal chamber 13 preferably also has one or more graduations to indicate fill level. Arm 13a of water seal chamber 13 is of smaller cross-sectional area than arm 13b, and communicates with collection chamber 12 via structure 113 and port 111. Disposed at the top of arm 13a of the water seal chamber 13 is an improved automatically releasing float valve 60. The float valve 60 allows the patient to draw high vacuum in the collection chamber 12 for breathing while automatically releasing when an excessive vacuum is maintained for an extended period of time. As will be discussed in greater detail herein below, the float valve 60 enables the vessel 10 to preserve the sterility of the fluid collected from a patient.

The upper end of arm 13b has a vacuum port 18 for connection to a source of vacuum. Water seal chamber 13 communicates with arm 14a of manometer chamber 14 through port 114. Arm 14b of manometer chamber 14 opens to the atmosphere through vented plug 15, which fits into a funnel-shaped recess and is removable to allow filling of manometer chamber 14 with water. Manometer chamber 14 is preferably provided with graduated markings to indicate fill level. Arms 14a and 14b communicate via the narrow slits 109 in bubble indicator 110. The manometer chamber regulates vacuum by allowing air at atmospheric pressure to be drawn through the manometer water column and bubble indicator into the suction outlet 18 at the top of the water seal chamber. The amount of water disposed in manometer chamber 14 serves to regulate the subatmospheric pressure present at the top of seal column 13b, and applied via the water seal to chamber 12. Specifically, when a vacuum source is connected to port 18, the subatmospheric pressure difference in the region of port 114 will under normal operating conditions be equal to the height in centimeters of the water column in arm 14a.

Certain respiratory conditions can cause a sudden increase in pressure within the pleural cavity. For example, a cough or an air leak into the pleural cavity can produce a substantially higher pressure within the pleural cavity; such pressure must be relieved to permit normal respiratory function. Additionally, such a sudden increase in pressure is passed directly to the drain device by tube 26, and in a prior art device can force water out of the manometer chamber through vented plug 15. This is undesirable, since upon return to lower pressure in the pleural cavity, a substantially lower vacuum will be imposed on the cavity due to the lower remaining water volume in the manometer chamber. The device 10 avoids this problem in part by providing, in addition to the aforesaid port and water column structure, a self-regulating positive pressure release valve which may be located in the vacuum line attached to port 18, in a wall of body 10, or elsewhere.

Near the bottom section of collection chamber 12 is disposed a fluid removal port 19. The port may include a microemboli filter, e.g., a 20–40 micron filter when direct reinfusion of collected blood is desired. Tubing is attached to port 19 and is fitted with a conventional clamp or sterile spike connector fitting to couple flow of fluid from chamber 12 into an infusion pump 28 (FIG. 2) or a transfer/infusion vessel as shown in FIG. 3 of the aforesaid U.S. patent application Ser. No. 556,022.

Figure 2:
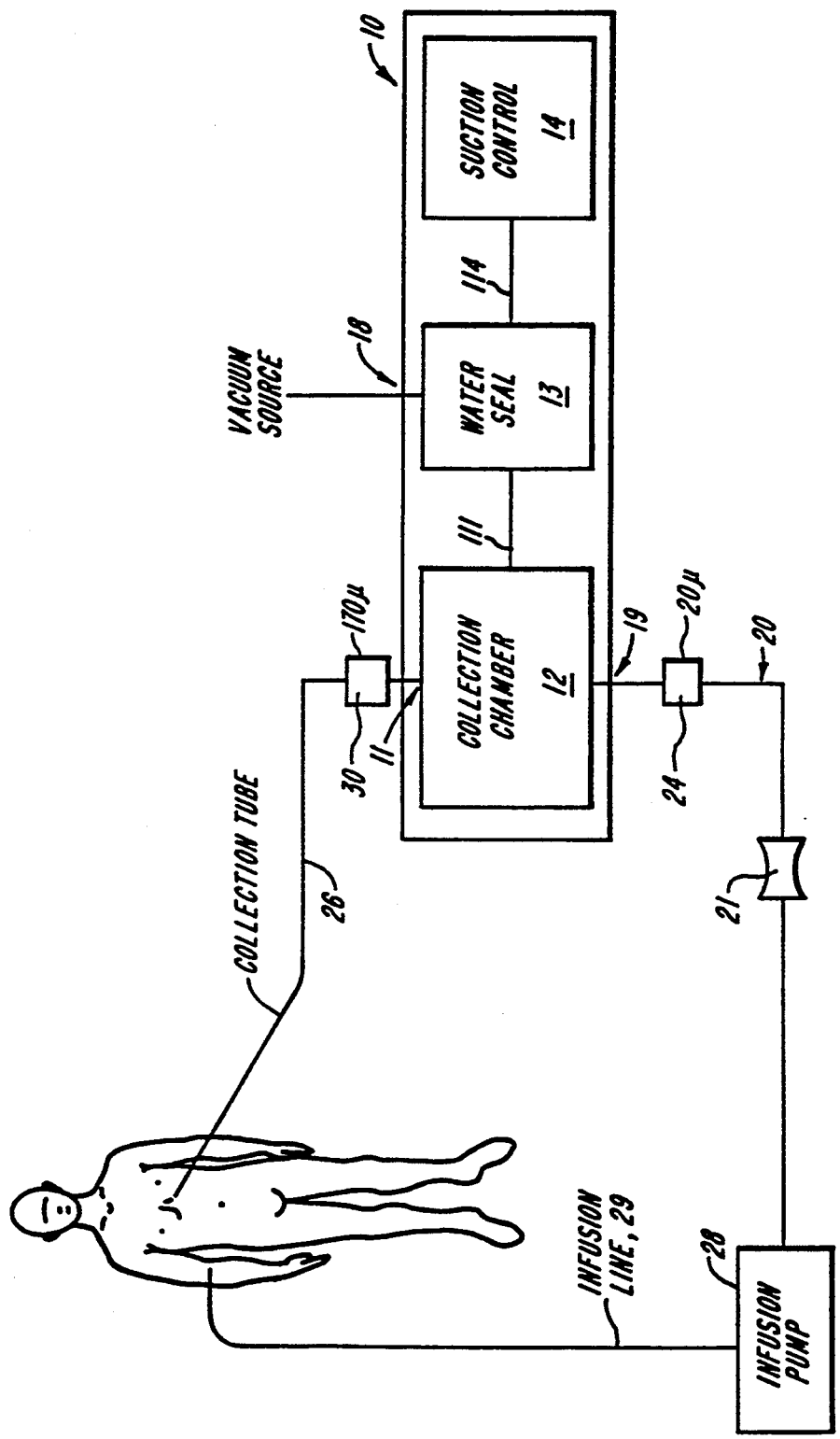
FIG. 2 is a schematic diagram showing an autotransfusion circuit according to the present invention.
Figure 3:
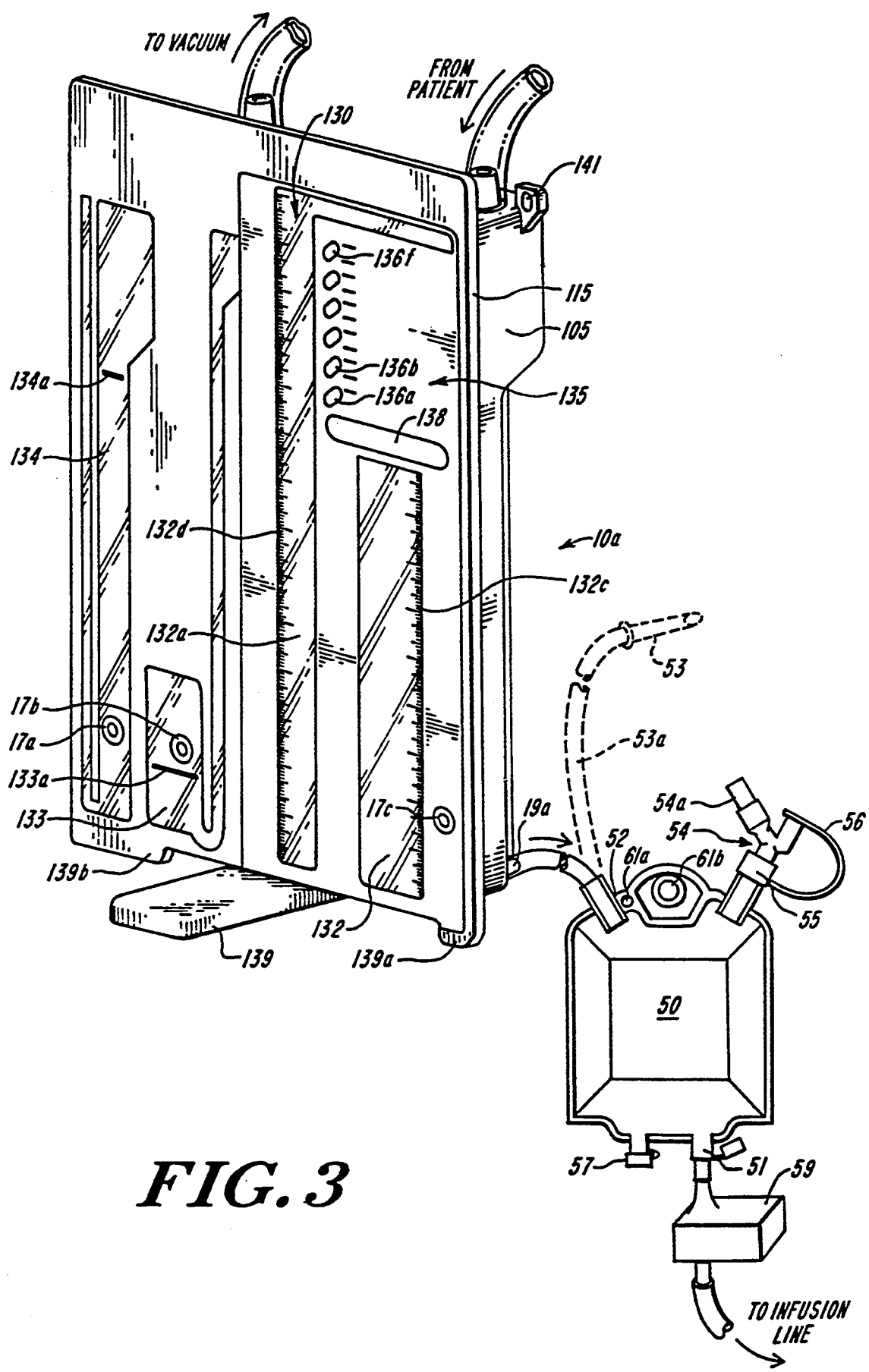
FIG. 3 is a front perspective view of an assembled system having the body of FIG. 1 for implementing an autotransfusion circuit similar to that of FIG. 2.

Operation of the drain apparatus is best understood with reference to FIG. 2, a schematic of an autotransfusion circuit utilizing the invention. In use, water seal chamber 13 is filled with water to a preselected level, and manometer chamber 14 is filled with water to a level corresponding to a desired subatmospheric pressure. Thoracotomy tube 26 is connected to the patient and to port 11, and vacuum from a wall outlet or portable vacuum source is then applied to vacuum port 18. Vacuum modulated by air bled in through the manometer chamber is thereby applied to the collection chamber 12, and to the thoracotomy tube 26, and fluids such as blood are drawn into collection chamber 12. Such collection may be utilized in the emergency room, operating room, intensive care or other post operative settings.

When used intra-operatively, a conventional suction head (not shown) is sealed to the distal end of tube 26, and the surgeon periodically vacuums the patient's blood from the site of the incision. When used post-operatively, the thoracotomy tube 26 is implanted in a suitable location in the patient's body cavity, typically the pleural cavity, and fluid is withdrawn as it collects while a subatmospheric pressure compatible with normal breathing is maintained in the pleural cavity and in collection chamber 12.

Body fluids entering chamber 12 pass through filter 30 which traps particulate matter, assuring that the liquids collected in chamber 12 are free of macroscopic particles. Irregularities of the pressure in chamber 12 caused by coughing of the patient or "milking" of the thoracotomy tube 26 are accommodated automatically in the device by changes in water levels within the columns 13a, 13b of the water seal chamber 13. Fluctuations in the vacuum source attached to port 18 are modulated by the water in the manometer chamber 14 and positive pressure relief valve 16 which automatically permit influx or reflux of air as required to maintain internal subatmospheric pressure in the narrow range corresponding to the water columns.

In the system of FIG. 2, autotransfusion may be accomplished by opening clamp 21, thus permitting fluid to flow out through filter 24, port 19, along line 20, and into infusion pump 28, which returns fluids to the patient via infusion line 29.

Referring again to FIG. 1, the present invention allows for automatic regulation of negativity during autotransfusion by virtue of the cooperation of port structure 111 including wall openings 111a, 111b through which water seal chamber 13 communicates with collection chamber 12, elements 113a and 113b of baffled drip-return or self-bailing structure 113, and the automatically releasing float valve 60. As fluid is autotransfused through port 19, subatmospheric pressure in chambers 12 and 13 as generated by the vacuum source and the egress through port 19 of the fluid from the collection chamber 12 are equalized through port 111 as air passes upwardly through chamber 13a. During normal operation, i.e., when water seal column height is less than approximately 25 cm of $H_2O$, seal integrity is maintained by the structures 113, 60 which prevent interchamber siphoning. Water rising as a column in chamber 13a and entrained as a mist in air bubbles passing through the column is confined in the impound volume 64 defined by valve seat 61 and the structure 113 and returned to the water seal chamber through a seat aperture 62. Similarly, elements 112a through 112d protect manometer integrity by preventing interchamber siphoning effects between the manometer and water seal chambers. In addition, a small float ball (not shown) rides in the column 13a between limit pins 13c, 13d and is dimensioned to partially obstruct the column when driven against either one of the limit pins. This slows movement of the stream of fluid under conditions of pressure bursts.

When, either due to stripping or milking of the tube 26, or due to the suctioning of fluid out of the collection chamber 12 for autotransfusion, there arises an excessive vacuum in chamber 12 such that the water column in chamber 13a reaches the float valve 60, the float valve 60 insures that sufficient vacuum is maintained in chamber 12 for an adequate, but not too long period of time. Typically, the float valve 60 will be positioned in the chamber 13a so that a water column of approximately 25 cm activates the float.

Figure 4B:
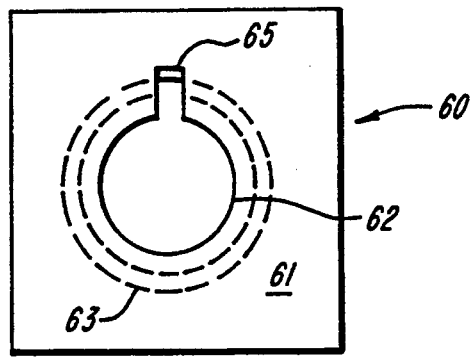
FIG. 4b is a top view of the float valve of FIG. 1.
Figure 4A:
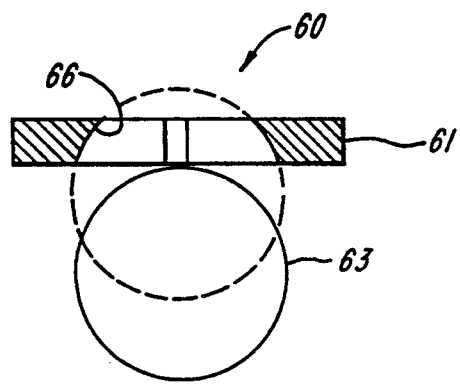
FIG. 4a is an enlarged cross-sectional view of the float valve of FIG. 1.
Figure 4C:
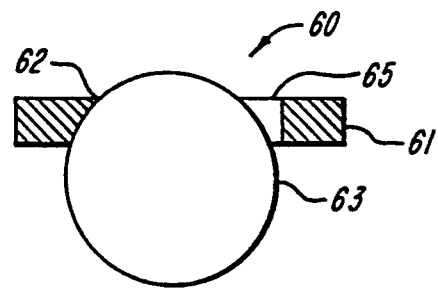

As shown in FIGS. 4a–c the float valve 60 includes a valve seat 61 and a ball 63. While a ball is shown in the figures, floats of other geometrics such as, for example, a cylinder, are equally suitable. The valve seat 61 defines an aperture 62 having an edge 66 which in a preferred embodiment is bevelled. The aperture 62 is shaped so that when it is engaged by the ball 63, water can still pass through but at a substantially reduced rate. Illustratively, the aperture 62 is shaped as a circle in communication with a notch 65. The aperture 62 has a diameter smaller than that of the ball 63 so that when the water level in chamber 13a reaches the float valve 60 the ball 63, having a density of less than one, is buoyantly urged into the aperture 65 and prevents free flow of water into the collection chamber 12.

The beveled edge 66 of the aperture 62 facilitates release of the float valve 60 when the fluid column can no longer support the ball 63. Additionally, by placing the valve seat 61 at a height of 25 cm, higher than is done with known float valves, and using a smaller quantity of water in the water seal chamber 13, an extended period of excessive vacuum causes depletion of the water column by water passing through the aperture 62 and results in the float valve 60 releasing. Accordingly, the float valve 60 accommodates the different fluctuations occurring during simultaneous auto-infusion of fluids and collection of fluids and prevents water siphoning from chamber 13a into the collection chamber 12 during normal pressure fluctuations, further protecting the patient from excessive vacuum by providing automatic release.

Of course, while a float valve is depicted, other valves that permit the free passage of air but impede without entirely stopping the passage of water can be used. A porous hydrophobic filter, for example, can be positioned in the chamber 13a so that air, but not water, from chamber 13a freely passes to collection chamber 12. Such a filter would have a cross-sectional area of from approximately 1 cm$^2$ to approximately 20 cm$^2$, depending on the dimensions of chamber 13a, with pores ranging in size from approximately ½ micron to approximately 100 microns. In this manner, as relatively low pressure in collection chamber 12 causes the water column in chamber 13a to rise, air on top of the water column will freely pass into the collection chamber 12. Once the water level reaches the valve, vacuum will be maintained in the collection chamber 12 as the flow of water from the water seal chamber 13 is impeded. Eventually, however, an extended period of excessive vacuum in collection chamber 12 will result in substantially all of the water in the water seal chamber 13 passing through the porous filter and into the collection chamber 12. At this point, air will move from column 13b to column 13a, and be allowed to pass freely through the porous filter and into the collection chamber 12.

For intraoperative use, suction can be controlled via a wall outlet regulator, or via manometer chamber 14. In any case, use of the device in this manner provides more gentle suction levels than those attainable by prior art intraoperative drain systems.

When used in this fashion collected fluids can be reinfused on a continuous basis directly back into the patient through filter 24 and infusion pump 28, because the gentle and continuous suction automatically provided by drain 10 minimizes damage to blood cells, and is compatible with the simultaneous outflow and inflow of blood from collection chamber 12.

FIG. 3 shows a non-mechanical autologous blood collection and infusion system, and better illustrates the drain of FIG. 1 fully assembled with its face plate 100 in typical operation.

The assembled drain unit 10a employing a body identical or substantially similar to the device of FIG. 1 has an outlet 19a at the base of its collection chamber 12 to which a transfer vessel 50 is connected via a spike connector, quick connect or direct tubing to receive fluids collected from a patent. Transfer vessel 50 is a heavy plastic bag having an inlet 52, and an outlet 51, as well as a vent 54 having a microporous filter 55 and closure cap 56. Inlet 52 and outlet 51 are at opposed ends of the bag, with the top/bottom orientation defined by a hole 61b for hanging the bag in a vertical orientation. A pierceable sampling or medication injection port 57 is preferably also provided.

At the bottom of vessel 50 a separate microemboli filter 59 is interconnected between port 51 and an infusion line. Shown in phantom is a spike connector 53 and large bore PVC infusion tubing 53a which, in the preferred embodiment, are permanently connected to inlet 52 and adapted to couple with a mating diaphragm closure and spike-compatible connector extending from the outlet port 19a of the drain 10a. Before interconnection of the drain and transfer vessel, connector 53 is maintained in a sterile state in a sheath 54a formed on the vent manifold 54.

Transfer vessel 50 is adapted to generate its own suction, and preferably is a spring-loaded suction vessel, having an internal structure of the type, for example, which is illustrated in U.S. Pat. No. 4,429,643. For purposes of describing the conventional aspects of this vessel, the disclosure of that patent is hereby incorporated herein by reference. That patent shows a bag with an internal folding frame which is urged apart by a coil spring to exert a force on opposite sides of the bag, creating a strong and substantially uniform level of suction therein. An embodiment of that patented spring-loaded suction vessel is presently marketed by the Johnson and Johnson Company as its "J-VAC" suction reservoir. In that device, a folding box-like internal frame placed about a coil spring is normally maintained in a substantially flat position by an internal latch. When the frame is slightly bent, the latch mechanism releases, and opposing walls of the frame are thereafter urged to unfold under the influence of the spring, creating an effective suction of 0.05 to 0.10 atmospheres.

For the practice of this invention, the precise suction level is not important, so long as it is sufficient to overcome the draw of collection chamber 12. An appropriate vessel is achieved by modifying the above-described commercially available suction vessel to further incorporate a capped and filtered vent, a capped outlet port vertically opposed to the vent, and preferably also a sampling port as shown in FIG. 3. In addition, the internal spring is suitably treated to meet USP blood compatibility specifications for contacting blood which is to be reinfused, and blood-compatible polymers or coatings are used for the internal frame structure as well as the bag inner surface. For the particular transfer vessel described, the level of suction developed by the vessel, corresponding to a water column of twenty to fifty centimeters, is sufficiently stronger than the levels maintained in drain 10a, to readily draw out any fluids from the collection chamber 12 of the drain. The suction differential remains effective to drain the collector 10a when transfer vessel 50 is suspended at any height approximately level with or below the top of drain 10a.

Operation of the system for collecting fluids and reinfusing the collected fluids proceeds as follows. First, the drain 10a is set up by filling the manometer and water seal chambers to an appropriate level for achieving the desired suction. This level will depend on whether the device is used intra-operatively, or, if post-operatively, on the nature of the thoracic drainage site and whether there is leakage into the thoracic cavity. Next, the vacuum source is connected, and then the drain line to the patient is connected. During this period, the outlet port is closed, or, if vessel 50 is connected, the port may be open so long as all vents and outlets of vessel 50 are closed and its spring mechanism is latched in the retracted position.

When a sufficient volume of blood for reinfusion has collected, vessel 50, if not already attached, is attached and its spring mechanism released. This draws the collected blood through port 19a from drain 10a into vessel 50.

Thereafter, the line from the drain outlet port is clamped, and vessel 50 is removed and its inlet is closed. The outlet of vessel 50 is then connected through a microemboli filter to an infusion line, and its contents are redelivered to the patient. This may be accomplished by placing a pressure cuff about vessel 50 for bolus delivery. Alternatively, it may be accomplished by hanging the vessel at a suitable height above the patient, opening the filtered vent, and delivering the vessel contents by gravity infusion. Once disconnected, a second vessel 50 may be connected to receive a further unit of collected blood, and to similarly reinfuse the blood.

Figure 3A:
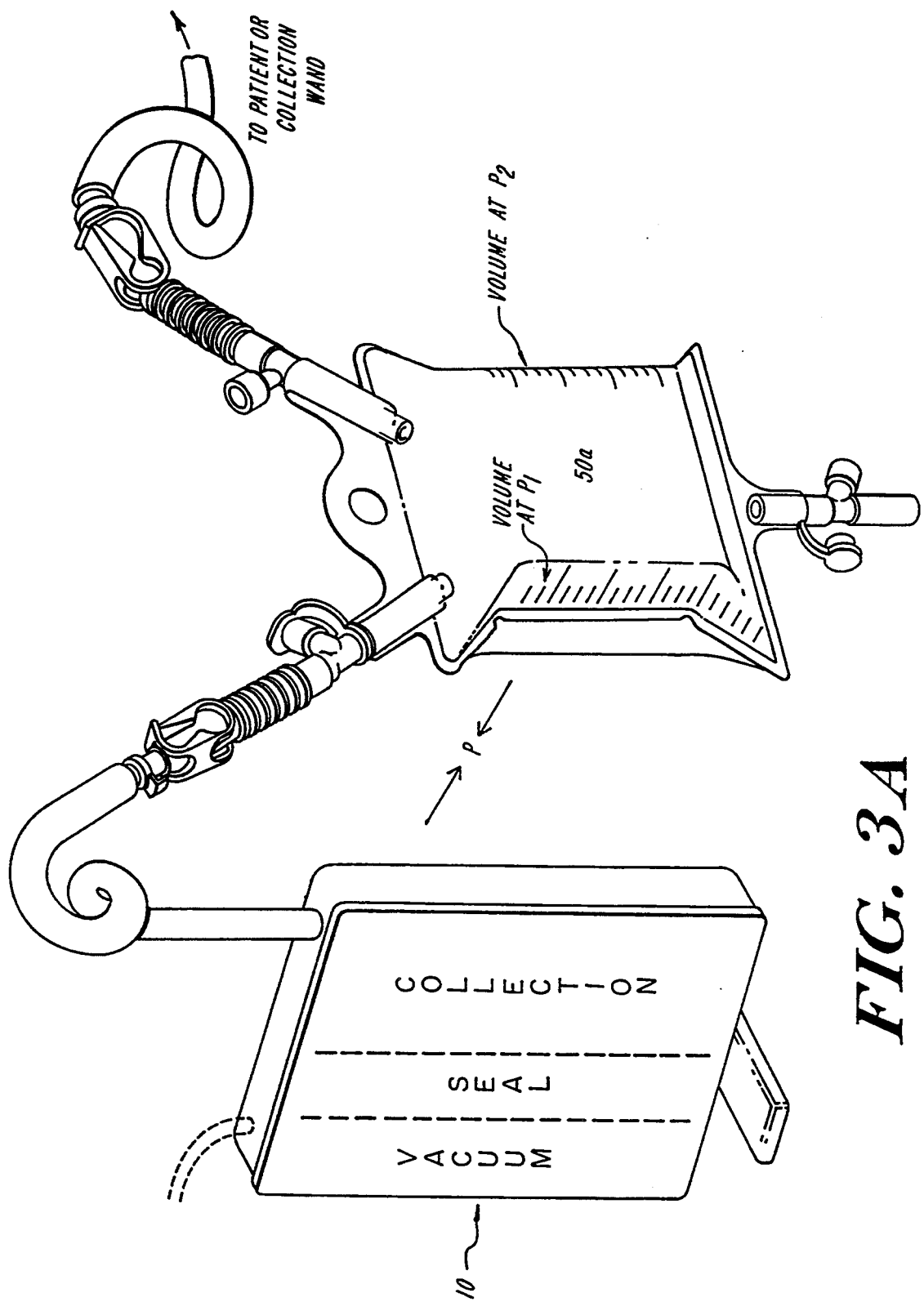
FIG. 3A is a perspective view of another implementation of an autotransfusion system, wherein components are arranged differently.

Another embodiment of the invention utilizes an in-line transfer vessel 50a as shown in FIG. 3A. This transfer vessel is removably placed into the patient drain line, between the patient and suction vessel 10, by quick connects, and thus serves to intercept blood. One or more such vessels may be used in-line in series, or may be successively placed in-line and removed when full, and thereafter suspended for operation as blood reinfusion bags. For this application the internal spring mechanism is opened initially so that the transfer vessel starts at normal atmospheric pressure. In that case, suction is provided solely by vessel 10, and the previously described internally stented spring structure serves to define a relatively fixed volume for the bag, that flexes and changes volume slightly to modulate abrupt changes in applied suction.

A more detailed description of such an embodiment is found in applicant's above-mentioned U.S. patent application Ser. No. 755,032, filed on Sep. 4, 1991 and entitled In-Line Fluid Recovery System. The entire contents of that patent application are hereby incorporated herein by reference, and the reader is referred thereto for a more complete description of this embodiment.

Returning to the drain 10a of FIG. 3, several features of the preferred embodiment are shown in the front perspective view, and are noted here before proceeding to a more detailed discussion of the interior shape of the preferred drain. Drain 10a is of a multichamber design wherein a unitary housing is formed of two portions. A molded rear or body portion 105 is preferably formed of a light-colored opaque plastic, and contains a number of baffles, walls and posts which extend to a common front plane and define the internal structure of chambers, ribs, ports and supporting elements much as previously discussed in relation to FIG. 1. Front panel 115 is formed of a transparent sheet of substantially uniform thickness. The body portion and the front panel are preferably assembled by linear vibration welding. For this purpose, slight protruding ridges may be formed in the inner face of the front panel to align with and seal to the linear wall portions of the body securely. The front panel, as illustrated, has a graphic mask 130 printed thereon defining a plurality of windows, status indicators and calibration or measuring indicators.

Among the "windows" defined by graphic mask 30 are a manometer window 134, a water seal window 33, and a collection chamber window 132, each of which is aligned over the corresponding chamber of the housing. Preferably fill lines 134a, 133a in the windows mark the appropriate water level to achieve a suitable suction level and water seal. In the illustrated embodiment, an additional window 132a is aligned over a second fluid collection column, which as discussed in greater detail below, is preferably at least partially isolated from the normal inlet-filtration-outlet circuit. Each of the windows preferably has a grommet port 17a, 17b, 17c which may be used, in the case of windows 133, 134 to fill or replenish the water column, and in the case of window 132 to sample the collected fluid.

In addition to the aforesaid window structures, the graphic overlay 130 includes an opaque region 135 which, as described in greater detail in regard to FIG. 4, covers a portion of the drain having a large area gross blood filter, through which fluids drained from the patient fall to reach the collection chamber. Preferably, opaque region 135, or one of the columns or regions below it, contains a printed chart, e.g., a set of blank lines against a light matte ground, to write a schedule of fluid recovery, or a record of fluids transferred to a vessel 50 or to an infusion conduit. In opaque region 135 a series of small clear windows 136a–136f provide an indication of the level of fluid accumulated inside the drain over the gross filter, as described below, of which the general location and shape is indicated at 138. The level indicated by windows 136a–136f depends on the rate of blood collection, and on the volume of accumulated clots. When the level continues to rise, unfiltered blood overflows into the column of window 132b.

A pedestal 139 is rotatably attached to housing 105, and rotates out from the general plane of the drain device to provide a stabilizing base to support the drain upright on a surface. An alternate means of support, provided in addition to the pedestal, is provided by a pair of hooks attached to a pair of brackets 141 (of which one is visible in the figure). These are J-hooks, useful for hanging the drain from a frame.

It will be observed that each of windows 133, 134 has a narrow and a wide portion. These portions lie over narrow and wide arms of the respective water columns. Another feature visible in FIG. 3 is that the housing of drain 10a is not of uniform front-to-back depth. For example, it will be seen that outlet 19a is located in a lower portion of the drain having a chamber thickness approximately half that of the upper portion. This geometry of differing chamber depths efficiently channels fluid to a lower collecting sump region. Other localized differences in a chamber depth or thickness, described in greater detail below, cooperate to provide a stable and highly uniform suction drain device.

Figure 5:
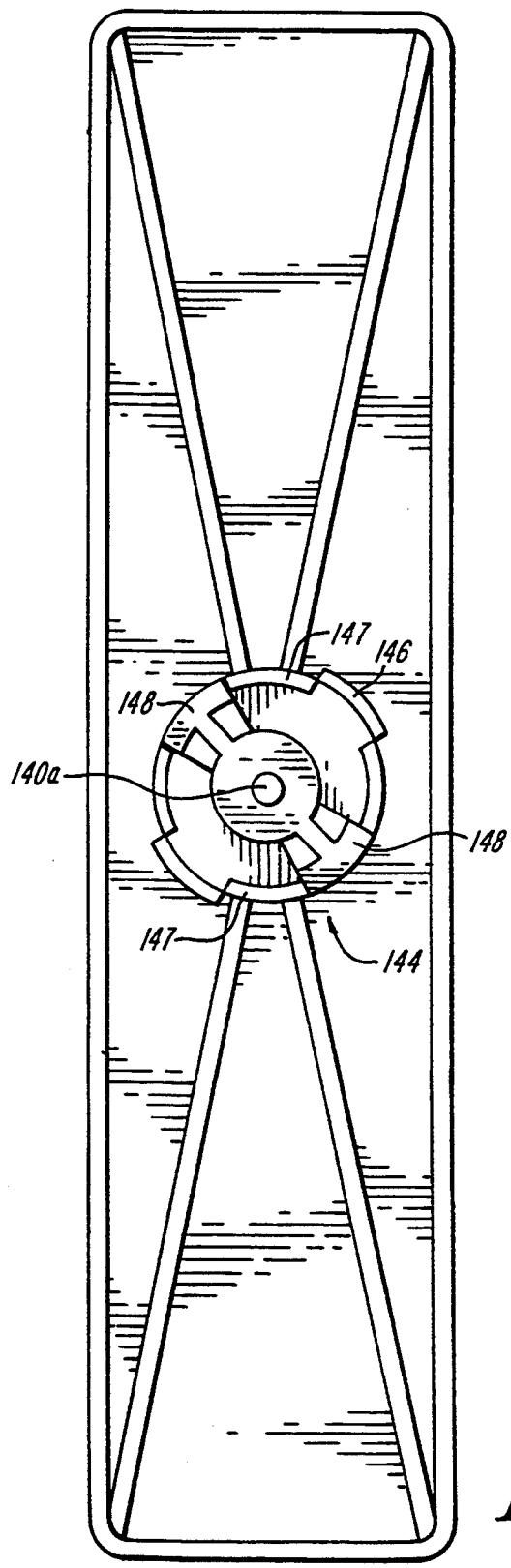
FIG. 5 is a bottom view of a pedestal for the drain device shown in FIG. 1 or 3.

Before proceeding to a detailed discussion of the different chamber geometries and their function, however, several features of the preferred embodiment of FIG. 1 will be described in greater detail. Returning to that Figure, a post-and-clip pedestal mounting structure 140 extends from the bottom of the molded body, and comprises a central turning axle or post 141, surrounded by two arcuate clips 142. Each clip 142 consists of a projecting body portion shaped like a partial segment of revolution of a cylinder, and a laterally extending tooth or claw 143. This structure fits into a matching opening 144 in a swing-out pedestal or stand 139, which is shown in bottom view of FIG. 5.

The extending claws 143 of each clip fit into keyhole openings 146a in the pedestal mounting hole, and rotate while bearing against a thrust face 147 that extends in an arc between protruding stops 148 as the pedestal is turned into an operative support position normal to the plane of the face plate. The post 141 fits into a central hole 141a of the pedestal. In use, if the pedestal and drain are wrenched in a manner that might cause one or both of the claws 143 to break off, the post simply flexes, and remains intact to assure that the drain remains standing rather than falling off the pedestal. The post thus serves as an auxiliary support coupling that accommodates bending stresses without failing, and which maintains the pedestal centered and oriented so that a single clip 142 can continue to maintain the pedestal connection. Axle 141 and clips 142 are integrally molded with the body portion.

Also integrally molded with the body portion is a small valve housing 116 extending upwardly from the top surface of the body at the top of manometer column 146, just adjacent to the passage 114 that leads to the suction inlet 18 and seal column 13b. A passage extends vertically through the housing 116, and a check ball is centered in the passage by edge tabs or centering nubs 117. The housing 116 opens forwardly, toward the face plate, and once the check ball is inserted therein, the device is closed by simply placing the flat face plate over the body.

In practice, applicant has found that the assembly of the face plate to the molded body is best performed by linear vibration welding. This joins the structure without glue or solvent. Thus the entire positive pressure relief valve structure is assembled by inserting the check ball and then assembling the face place onto the body, using a total of one additional part (the ball) and one assembly step, insertion of the ball. Alternate valve structures on shapes using a flap rather than a ball valve are also possible with the integral apertured housing 116.

A second and related valve structure is also provided for an excess negativity valve, denoted generally by 118 in FIG. 1. This structure is concealed by the face plate after assembly, and thus is not visible in FIG. 3. As best seen in the top perspective view of FIG. 7C, the valve structure 118 includes a small upward extension 118a of the body defining a valve housing that has a laterally-directed opening 118b extending therethrough in communication with a large central chamber enclosed by the extension 118a, and indicated in phantom. A small collateral chamber 118c communicates with the central chamber. Both the central chamber and collateral chamber 118c are closed by the face plate 100 so that a passage from the interior of body 10 communicates with the surrounding atmosphere through the two chambers.

Figure 7A:
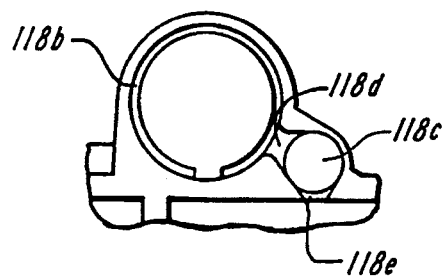
FIGS. 7A-D show views of the integral valve structures of the drain device shown in FIG. 1.
Figure 7B:
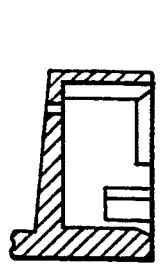
Figure 7C:
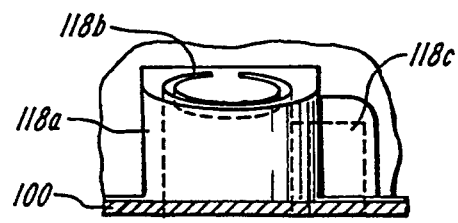

As shown in the front elevational detail view of FIG. 7A, the central chamber of the valve housing 118a has a first aperture 118b opening to the outside via the units back wall, and a second aperture 118d communicating with the collateral chamber 118c. Chamber 118c in turn has a further aperture 110e which extends through to the interior of the vessel housing, at the top of the small arm 13a of the water seal (FIG. 1) adjacent the passage to the collection chamber 12. The illustrated central and collateral chambers each have the form of a horizontally disposed cylindrical bore. A filter plug is placed in chamber 118c to assure that any air allowed through the valve housing is free of contaminants. In the central chamber a relatively stiff elastomeric disc is inserted to cover the first aperture 118b, and a coil compression spring is then placed in the chamber to seat against the face plate and press the disc against the aperture and close it. Face plate 100 secures the valve and filter elements in the housing, and closes the open faces so that the only path through the valve structure is the series path between openings 118b, 118d and 118e. Aperture 118b is a C-shaped opening defining a central tab, which when pressed by the attendant unseats the disc and allows airflow past the disc, through the filter and into the vessel. FIG. 7B is a vertical section along a front-to-back plane through housing 118a, showing the general shape of the valve-defining wall. Advantageously, valve 118 is located at the top of the water seal chamber, and does not introduce air directly into the collection chamber.

Figure 7D:
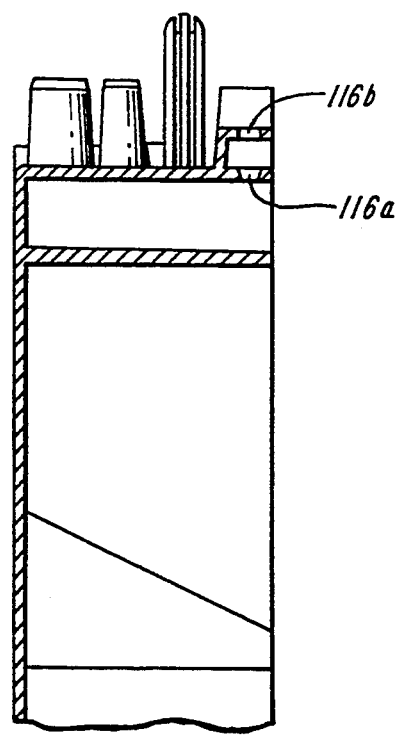

By way of completeness, FIG. 7D shows a corresponding section, to approximately the same scale as FIG. 1, through the valve 116. In that valve, a ball seating aperture 116a communicating to the vessel interior, and a vent 116b opening to the atmosphere, are both vertically oriented. A small plastic ball seats against the face of aperture 116a, and rises in response to increased pressure to relieve that pressure. While a spring and flap or related structure may be substituted for the ball, the illustrated construction has the advantage of involving a single self-aligning part, the check ball, which is automatically secured by the installation of face plate 100.

Figure 8:
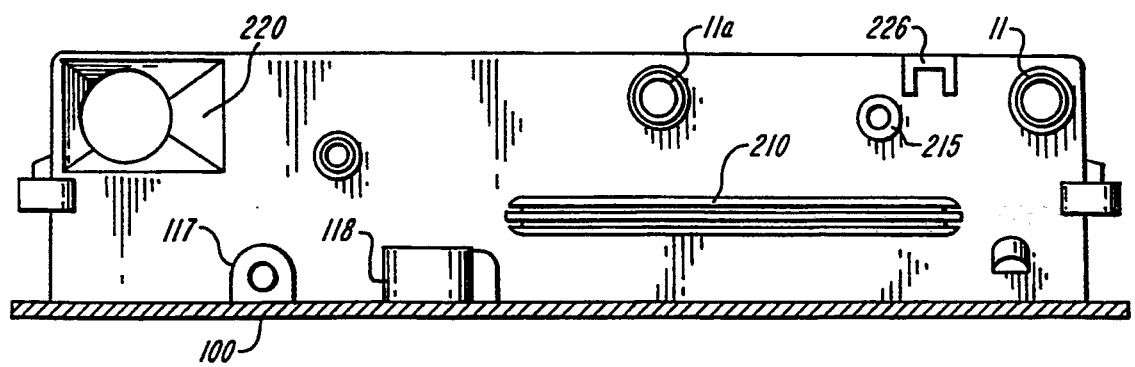
FIG. 8 is a top view of the drain device.
Figure 11:
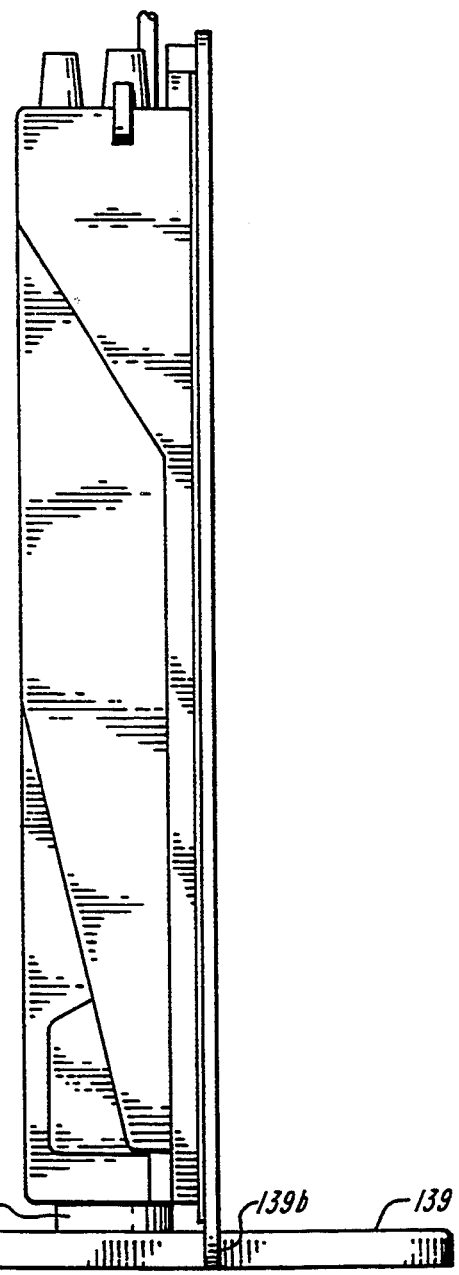
FIG. 11 is a side view from the manometer chamber side of that drain device.

In addition to the foregoing novel features of the drain of the present invention, the molded body 10 incorporates a number of useful improvements that contribute to its safe and effective operation, as best illustrated in the top view, FIG. 8, in conjunction with FIG. 1. Among these features are a handle 210, an injection port 215, a catch funnel structure 220, and a reinforced thumb boss 226 and knockout port 225. Each of these features will now be described in greater detail.

Handle 210 is integrally molded with the body portion, and is a simple inverted U-shape rod of about one quarter inch diameter, rising one and a quarter inches and with a width of approximately four inches. Handle 210 is approximately centered in a front-to-back position, taking into account the thickness of the face plate, but is off-center laterally, being located over the blood collection chamber 12. This assures that the drain is well balanced when fluid has been collected, and that the blood chamber will not tilt excessively downward when the device is lifted.

Significantly, the face plate extends upwards to the level of valve 118, approximately three quarters of an inch, so the handle actually protrudes beyond the top of the face plate by only a small amount, under one inch. Thus, the face plate serves as a protective baffle shielding the handle from being snared by dangling hooks, tubes or clothing.

Catchment funnel 220 is a truncated tetrahedral depression formed in the top surface of body 10 surrounding the vent opening. This catches any slight spillage that may occur when filling the manometer chamber.

Injection port 215 is a grommet or sealing septum port, like ports 17a–17c shown in FIG. 3. Unlike those ports, however, it is located in a horizontal surface of the body, and is positioned directly over the clot filter 30 in the collection chamber 12. Preferably, the port is positioned over the left (upward) side of filter 30, which is canted, as discussed further below. Port 215 is intended for the injection of anticoagulant or antibiotics. Its location provides an effective point of introduction to assure efficacious treatment of all collected blood and to inhibit clogging of the clot filter. With this location and orientation, the needle is aimed straight down, making it possible for the first time for an attendant to inject material using a single hand, without having to hold or stabilize the drain vessel in any way.

Returning now to FIG. 1, it will be seen to be essentially a sectional view of the molded rear body portion of the drain of FIG. 3, along a plane parallel to and slightly behind the front panel. To aid in visualizing the correspondence with features of FIG. 3, the fill lines 133a, 134a and grommets 17a, 17b, 17c are indicated on the Figure, although they are preferably features of the panel 100. The pierceable sample/fill grommets 17 may alternatively be located in apertures in the rear wall of the body portion in approximately the positions indicated in FIG. 1. Certain details of FIG. 1 are also intended as schematic rather than as exact sections. For example, the level indicating ball 330, described below, is simply shown in a perspective view for ease of understanding.

A principal feature of the illustrated device is that it achieves stable and safe suction levels despite changing conditions at the patient inlet port 11, or at the outlet/reinfusion port 19. To this end, the device includes the float valve 60 as described above, and the walls defining the three chambers and the passages therebetween have the following properties.

Manometer chamber 14 includes a two arm U-shaped water column wherein a first arm 14b which is open to the atmosphere via plug 15 has a cross-sectional area substantially below (e.g., less than one tenth) that of the maximum cross-section of the second arm 14a communicating with vacuum port 18. Such an arrangement limits the amount of water which can be drawn from column 14b into column 14a when suction starts, so that the resting height of the water column in column 14a is stable and accurately reflects the intended suction level. It further limits the amount of water which can be blown from column 14a into column 14b in the event of a pressure surge in the interior of the drain, so that short time pressure fluctuations are modulated by the expenditure of energy in pushing water along the column, and abrupt water losses which might disable the device do not occur. A third sub-chamber 14c communicates with arm 14a via lateral opening 14d in a divider wall 112f. This sub-chamber effectively doubles the fluid-holding capacity of the manometer chamber, yet is spaced out of the air flow path between the bubble-former 110 and the vacuum port 18, so that water in the sub-chamber is shielded from the evaporative losses due to airflow through chamber 14a which would otherwise regularly degrade the accuracy of the suction setting. This lateral subchamber arrangement stabilizes the suction level over the long term, as well as providing a larger buffer volume to prevent fluid loss from pressure back-surges.

A wall 112f that serves as a divider plate separates subchamber 14c from the essentially vertical column 14a, extending between face plate 100 and the back of the vessel. A slot 14d extends the full depth of the vessel through wall 112f to allow a relatively unhindered migration of water from chamber 14c back down into column 14a. Furthermore, the top of the divider plate 112f is angled back in region C starting at a fluid height of about twenty-two centimeters. Under normal operating conditions with a water column of approximately 20-25 centimeters, the fluid in column 14a is drawn upward with a vigorously bubbling motion, and spills over spillway C whence it returns, through the collateral chamber 14c and return slot 14d into the column 14a. This wave-like cycling of the upper portion of column 14a through chamber 14c has been found to harness the irregular bubbling disturbance into a relatively smooth flow circulation of the fluid in the upper part of the column, and thus provide a more uniform fluid level and suction operation, free of the extreme oscillations and vertical "hunting" that characterize the downstream arm of conventional manometer columns.

The plurality of curved baffles 112a-112c in the upper portion of the manometer chamber return spray and condensate to the water column, resulting in further effectiveness of fluid retention in the column.

Figure 10:
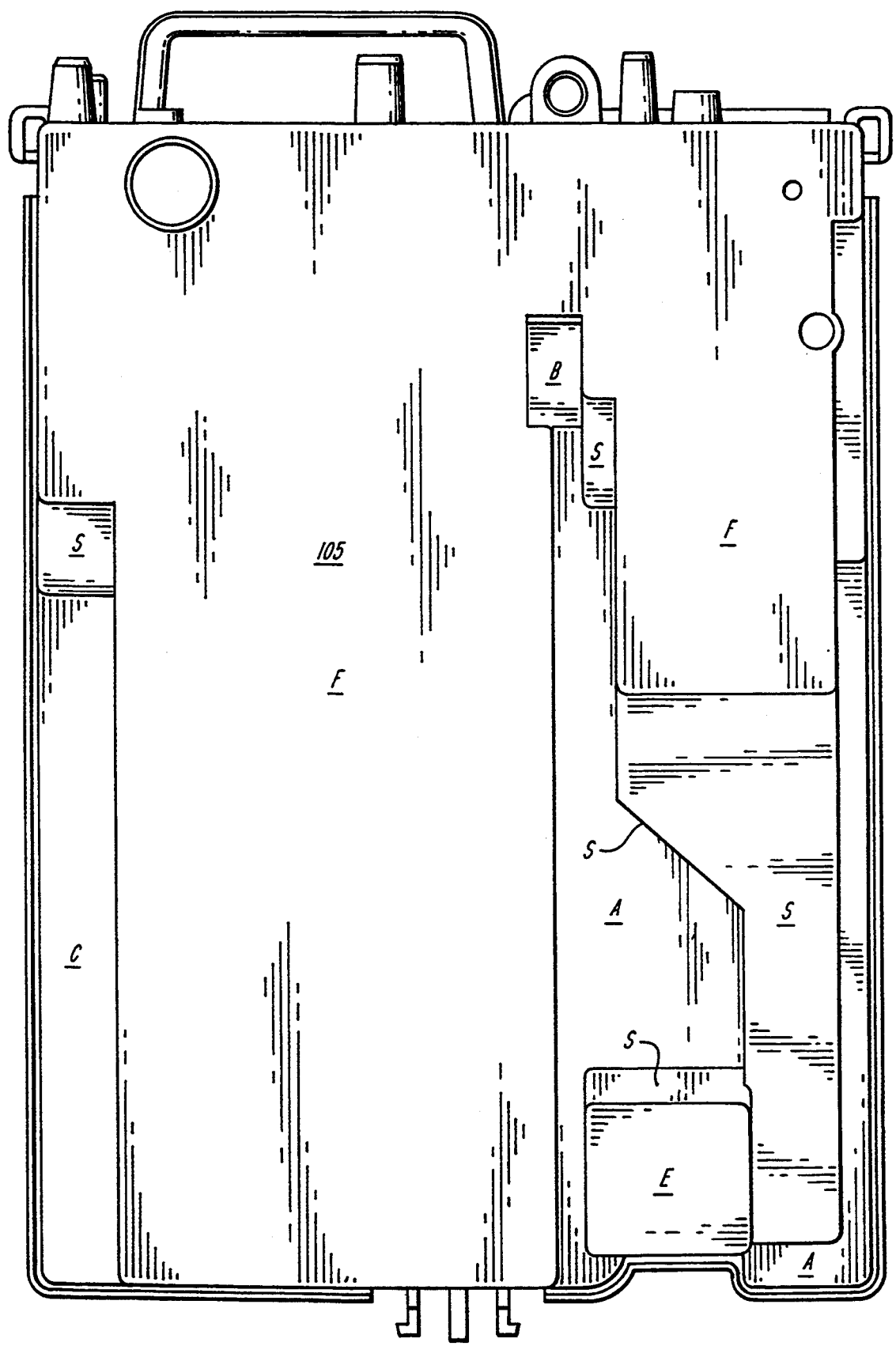
FIG. 10 is a back view of that drain device.

The baffle plate and side chamber may thus be seen as a structure for converting energy of fluid motion in the top of column 14a into a well regulated circulatory flow through the side chamber. One wall 14g of the side chamber angles downwardly toward opening 14d. Water following the wall is directed toward the return passage 14d, thus helping to initiate and maintain cyclic flow about the baffle. As shown in FIG. 10, the back wall of the side chamber and column is preferably also slanted inward.

Baffle plate 112f may also include a plurality of smaller openings disposed at locations in the middle portion of its height. In that case, as the size or number of these openings come to predominate over the size of the lower return opening 14d, the baffle structure increasingly serves to relieve pressure or damp oscillations in the vertical column by a more diffuse mechanism rather than to create a single cyclic flow loop. In all cases, however, the effect is to decrease hunting or surging of fluid and to stabilize the fluid column.

The volumes of water in the manometer chamber 14 required to achieve a given suction level in a prototype embodiment are set forth in the following table of manometer fill volumes. It will be seen that the relationship between desired suction pressure and required water volume is not linear. That is, higher suction levels require more than proportionately larger volume of water.

TABLE I

| Desired Suction Pressure | Approximate cc Volume |
| --- | --- |
| −20 cm H$_2$O | 320 cc |
| −15 | 155 cc |
| −10 | 55 cc |
| −5 | 20 cc |

The water seal chamber 13 similarly includes a pair of arms of imbalanced cross-sectional area, 13b, 13a with the smaller-section arm 13a communicating via a reflux structure 113a, a tortuous baffled path through staggered ports 111a, 111 to the blood collection chamber 12. As with the arms of the manometer chamber, the smaller arm 13a over its operative part preferably has a cross-sectional area which is ten percent or less of that of the largest, or pooling, region of the larger arm 13b. At the top of the arm 13a, however, the portion of the arm containing the reflux structure is enlarged to define an impound volume 64 above the float valve 60. In the event that an extreme underpressure condition should occur in the collection chamber 12, therefore, the fluid from arm 13b which passes through the aperture 62 may be accommodated within arm 13a and will not be drawn through ports 111, 111a into the collection chamber.

In the event that an excessive vacuum condition in collection chamber 12 causes a rush of water to be sucked up arm 13a toward the port 111, as discussed previously, the water's progress is stayed in large part by the float valve 60. In this manner, extreme pressure fluctuations can be accommodated in the collection chamber without disabling the entire drain device. Water which manages to pass through the float valve 60 is retained in the impound volume 64 and is prevented from mixing with fluids in the collection chamber 12. If the excessive vacuum condition is maintained in the chamber 12 for an extended period of time, a sufficient quantity of water passes through the float valve 60 to cause the float valve 60 to release, thereby relieving the excessive vacuum condition.

A level indicating ball 33 rides in column 13a between two permanent posts 13c, 13d formed in body portion, so that the level of the float provides an indication of an anomalous underpressure in chamber 12, visible through window 133 (FIG. 3). When an anomalously high suction in the collection chamber causes the level indicating ball 33 to reach the post 13d, any additional rise in the water level engages the float valve 60. If the high suction is maintained only for a short period characteristic of patient inspiration, the float valve 60 prevents any substantial reverse flow of fluid, and thus maintains the high suction in the collection chamber 12. If, however, the high suction is maintained for a dangerous period of time, i.e. longer than a patient breath-interval, water passing through the valve 60 reaches the impound volume 64. The weight of this water opens the valve 60 and relieves the suction. Also, the suction is automatically lowered by the passage of air from columns 13b, 13a.

Figure 6A:
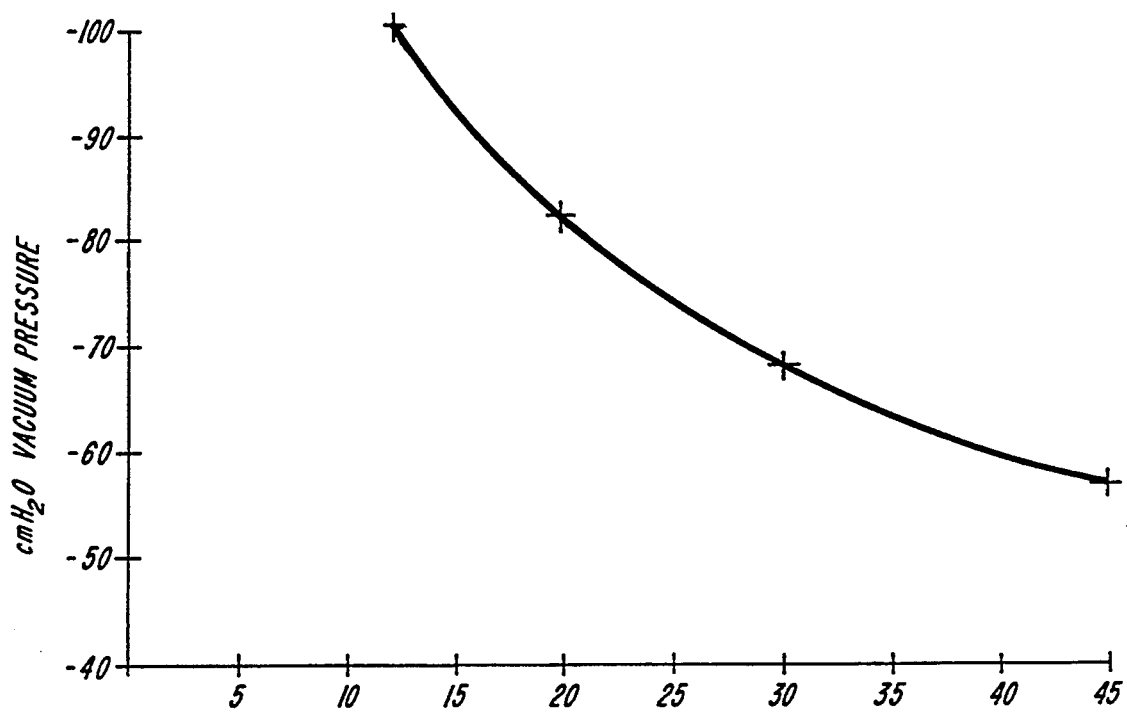
FIG. 6a is a graph representing the relationship between vacuum pressure in the collection chamber and valve release time.

FIG. 6a is a graph of the relationship between vacuum in the collection chamber 12 and the time required for the float valve 60 to release. As is shown by the graph, higher vacuum levels in the chamber 12 result in shorter release times. For purposes of illustration, assume that a normally slowly breathing patient will draw 10–12 breaths per minute. By dividing the lower value of this range by a safety factor of 2 (to assume, therefore, a rate of 5 breaths per minute) a maximum period of time for a held breath of 12 seconds is determined. Further, assume that at most a normally breathing patient can generate vacuum in the chamber 12 having a range of $-90$ to $-100$ cm of water. The chest drain of the present invention preferably has characteristics to allow the patient to maintain a vacuum level of $-90$ to $-100$ cm of water for a period of at most 12 seconds.

By reference to FIG. 6a, it can be seen that the float valve 60 releases at 12 seconds when a vacuum of $-100$ cm of water is maintained in the collection chamber 12. As discussed above, this allows the patient to breath. If, however, such a vacuum level is maintained for longer than 12 seconds, enough water will have passed through the notch 65 in the float valve 60 such that the water level in the column 13a supporting the ball 63 will be insufficient to maintain the ball in the seated position. The valve, therefore, will release. In this manner, dangerously high levels of vacuum that could result in damage to the patient's thoracic cavity are relieved without any intervention by hospital personnel.

Figure 6B:
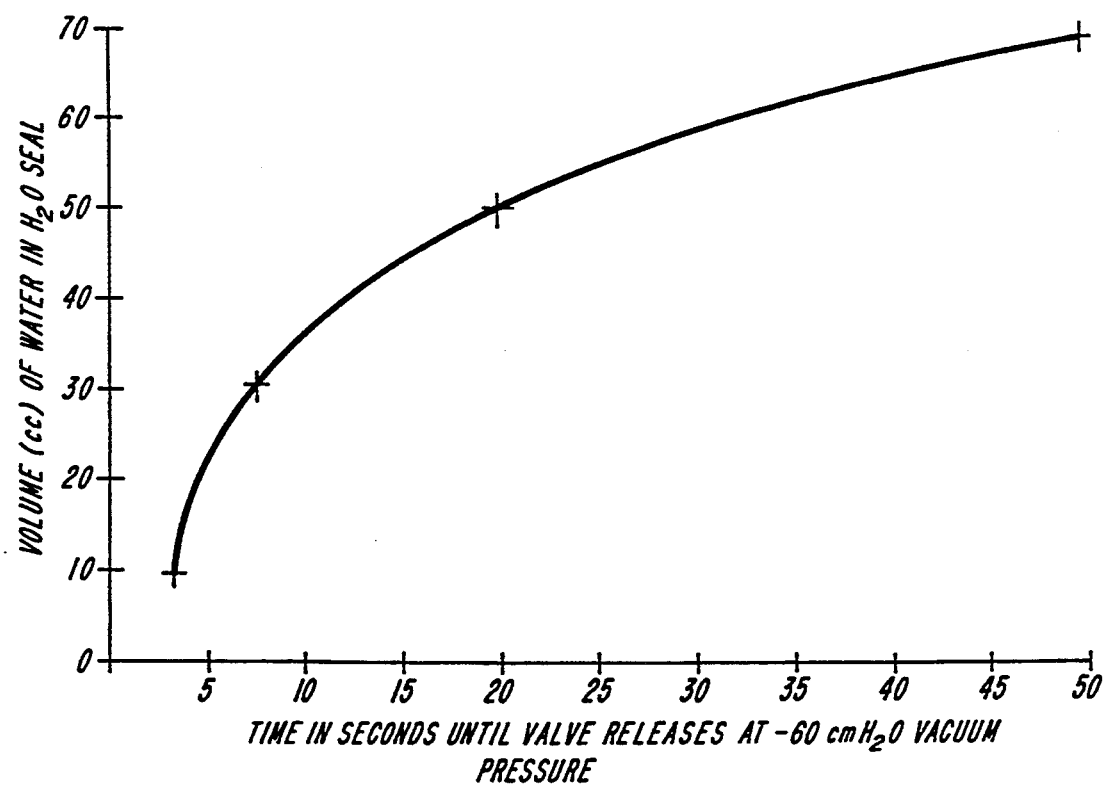
FIG. 6b is a graph representing the relationship between the volume of water in the water seal and valve release time when there is vacuum pressure in the collection chamber equal to $-60$ cm $H_2O$.

It is, therefore, a desirable characteristic of the present invention that the water volume in the water seal be selected to allow the float valve 60 to properly release. FIG. 6b is a graph of the relationship between the volume of water in the water seal and the time required for the float 60 to release when a suction level of $-60$ cm $H_2O$ is generated in the collection chamber 12. The graph shows that generally greater volumes of water in the water seal result in the float valve 60 requiring a longer period of time for release. Note that the curve asymptotically approaches a value of 70 cm of volume, representing a volume of water which will result in the float valve 60 effectively never releasing. Therefore, when the drain device is used for closed wound chest drainage, the water seal must never be filled with so much water.

FIG. 6b graphically illustrates that the float ball 63 is supported in the valve seat 61 by the column of water underneath it. That is, as water is drawn through the notch 65 in the valve seat 61 the water column beneath the ball 63 is depleted until it eventually can no longer support the ball in the valve seat 61. It can be understood, therefore, that larger volumes of water in the water seal will require longer periods of time to be depleted to this point, i.e. the point of valve release. In a preferred embodiment, the volume of water in the water seal chamber 313 will be between 25 and 65 cc of water. A volume of water of approximately 40 cc has been found to be particularly effective. Accordingly, if a vacuum of $-60$ cm of $H_2O$ is generated in the collection chamber 12, the float valve of 60 will release in between 5 and 50 seconds. This will be sufficient to allow a patient to breath, while prohibiting extended periods of exposure to dangerous vacuum levels. In this manner, the chest drain of the present invention is superior to known chest drains which have non-releasing check valves and require operator vacuum release through manual means.

It is also a desirable feature of the invention, that when the float valve 60 releases, the vacuum in the collection chamber 12 is returned to its pre-high vacuum event level. This is because no manual vent has been opened to expose the collection chamber 12 to atmospheric pressure. As a result, the amount of vacuum that the patient must generate for normal breathing will remain at acceptable levels.

The third major sub-chamber, the collection chamber portion 12, of this embodiment of the drain device is defined by outer contours of the molded body portion 10 as well as by an internal wall 335 which extends for the entire height of the drainage device. Wall 335 separates the collection chamber 12 from water seal 13, so that the two chambers communicate only at port 111 as described above. Port structure 111 includes a slot 111b about two millimeters tall extending the full five centimeter depth of the drain body, while a second port 111a located in a series path is less deep and has a cross-sectional area of approximately one square centimeter. The total volume enclosed by the body is approximately three liters, comparable to the volume of the pleural chamber. Of this amount, collection chamber 12 constitutes two or more liters. While the patient connection at port 11 is a large diameter thoracotomy tube which can transmit fairly abrupt pressure impulses to chamber 12, the two ports 111a, 111b limit the attainable flow rates and thus modulate pressure impulses which are initiated on either side of the port.

In addition, port 111a is located immediately adjacent the face plate. In the event the vessel is tipped backward, any water that reaches the impoundment chamber 64 will not rise to the level of port 111a, and thus cannot pass into the collection chamber.

In accordance with another aspect of the invention, between the chamber-defining wall 335 and the outer side wall 336, one or more partial or complete intermediate walls 337, 338, 339, 340 which are integrally formed with the housing body portion, separate chamber 12 into sub-chambers 12c and 12d as discussed below. Other wall segments or protrusions 351, 352 extending from the body, support a large-area fall-through filtration element 30 below inlet 11, and extend to an upper wall portion 340 that provides a sloping-floored impoundment for fluids which have not yet passed through the filtration element 30.

As shown, the fluids inlet 11 channels the incoming fluid so that it falls straight downward into the upper portion of the extreme right sub-chamber, onto filter 30. Filter 30 is advantageously mounted slanting downwardly to the right, for example, at an angle of about 15°, so that clots deposited in the filter slip down to the side and tend to block only the lower portion leaving the uphill filter area unclogged. Filtered blood then seeps through. This fall-through filter arrangement minimizes mechanical trauma to the blood. Filtration element 30 is a large area gross filter, such as a fabric or an open-pore sponge filter, which is effective to remove clots and gross particles from the incoming fluids. In a preferred embodiment, the filter material is a polyurethane foam sheet one half inch thick, of the type used in blood oxygenator apparatus, and has rectangular dimensions of $2\frac{1}{4} \times 3\frac{1}{2}$ inches. It may be treated with an anticoagulating agent to pre-process the fluids passing through it, or anticoagulant, antibiotic or other treatment fluids may be added through port 215, discussed above. The filtered fluids then pass to the lower portion of chamber 12. In lower portion 12, the back wall of the body angles forwardly to form a chamber of lesser front-to-back depth constituting a funneled collection sump at outlet port 19.

In operation when the drain receives an unusually large flow of fluids or the filter 30 becomes blocked with clots, the incoming fluids are impounded by the wall 340 and rise, to eventually overflow the upper walls. As they rise, the fluids contact a fresh area of the filter that has not been coated with clots, and through which they may once again pass at a relatively fast rate to the sump region and the outlet port. This arrangement promotes longer, more stable and effective operation of the filter.

Further, if the rate of fluid intake or amount of clots does cause the impounded fluids in the upper space to overflow, they pass over the top of wall 340. In that event, the fluids pass without being filtered into collection chamber 12. The level in the filter impoundment space is visible through the filter/flow status windows 136a–136f (FIG. 3), so that an excessive bleeding rate or the effects of an excessive clotting condition are made visible to hospital personnel. The provision of an open, fall-through filter in this manner prevents back-up of fluids in the thoracotomy inlet tube from the patient, a common cause of tamponade, while still providing pre-filtration of scavenged blood. This is a distinct improvement over a closed, e.g., sock-type filter as used in many prior art devices. It further removes the filter itself from the suction pathway, so that blood in the filter is not subjected to a dessicating draw of air.

Figure 15:
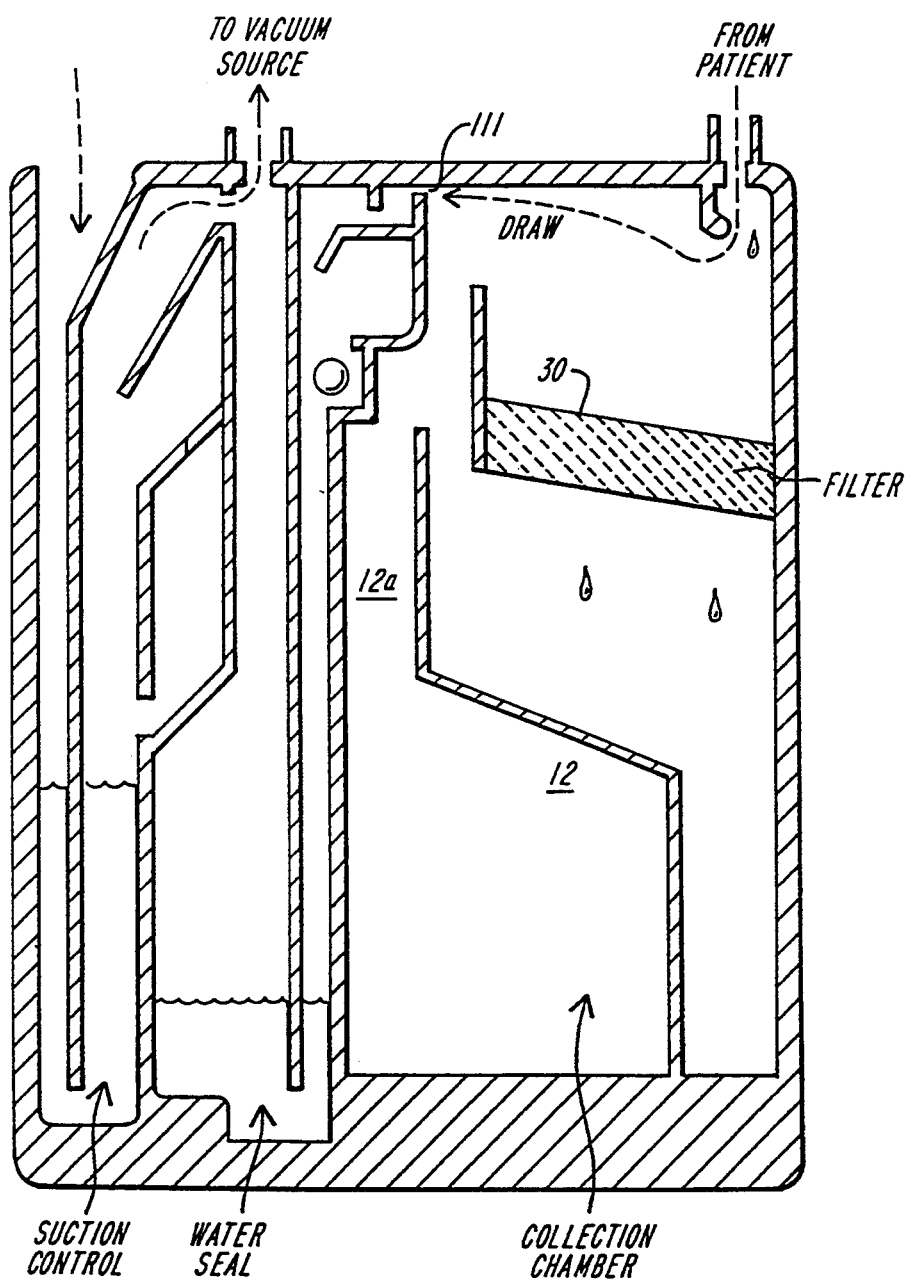
FIG. 15 illustrates interior flow isolation characteristics of the drain device of the present invention.

It will be seen that the structure of walls, baffles and ports just described results in the provision of a suction drain vessel wherein bidirectional pressure fluctuations are substantially compensated, and abrupt pressure impulses are modulated to more gradual perturbations that do not interrupt the functioning of the device. A further feature of note is that normal suction draws are established such that the diffusion path for contaminants to enter the collected blood is relatively isolated. FIG. 15 illustrates the normal directions of gas flow in a device like that of FIG. 1.

From the patient inlet 11, airflow, if any, is normally along the top of chamber 12, toward ports 111a, 111b. Blood entering at inlet 11 thus has a relatively low probability of encountering airborne contaminants, and it falls downward into chamber 12, where it is isolated from moving air by the relatively long chimney-shaped region 12a. Thus, in the rare event air from water seal column 13 is drawn past port structure 111, it is unlikely to result in significant contamination, and the collected blood will be safe for reinfusion for at least the duration of a typical surgical operation, similar procedure or bleeding event.

Figure 9A:
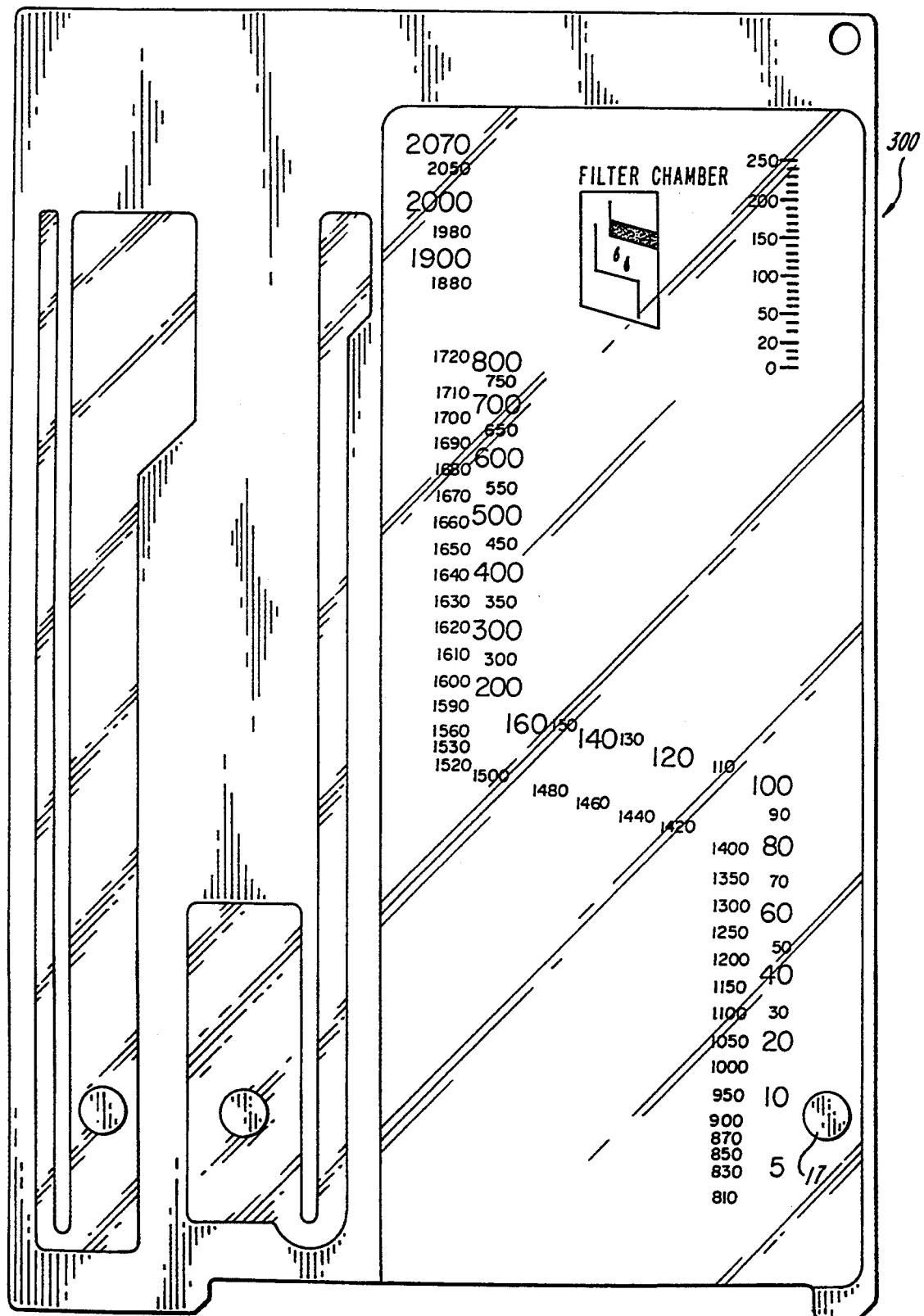
FIGS. 9A, 9B show front panel decals of drains having different wall dividers in the collection chamber.

The vertically extending wall comprised of segments 337, 338 and 339 in the configuration illustrated in FIG. 1 separates the collection chamber 12 into first and second chambers 12c and 12d, respectively. Chamber 12c may be characterized as primarily a high resolution low volume chamber. It will be seen to have the general form of a broad catchment funnel positioned below the filter 30 that channels all blood into a narrow neck portion extending above outlet 19. A collected volume of one hundred milliliters fills the neck to a depth of about fifteen centimeters, while the fluids do not run over the top of wall 337 into subchamber 12d until the collected volume exceeds 750 ml. FIG. 9A shows a typical front panel decal 300 for a drain having this wall configuration, showing the large graduation resolution of the right side blood collection chamber. This drain is suitable for monitoring low levels of bleeding that occur during recovery from thoracic surgery, or for use as a pediatric drain or volumetric reinfusion vessel.

By removing the lower wall portion at region 339, the height-to-volume characteristics of the collection vessel are transformed to ones more suitable for monitoring large blood losses, such as occur in cardiac surgery. This change is effected by a providing a removable mold block assembly in the mold used to form the body 10. The removable insert is solid, or fills the region between those mold blocks which normally form the wall 339 during the molding process, at least at the lower region thereof. This results in an opening through, or the entire absence of, wall 339 so that the regions 12c, 12d become one continuous collection chamber.

Figure 9B:
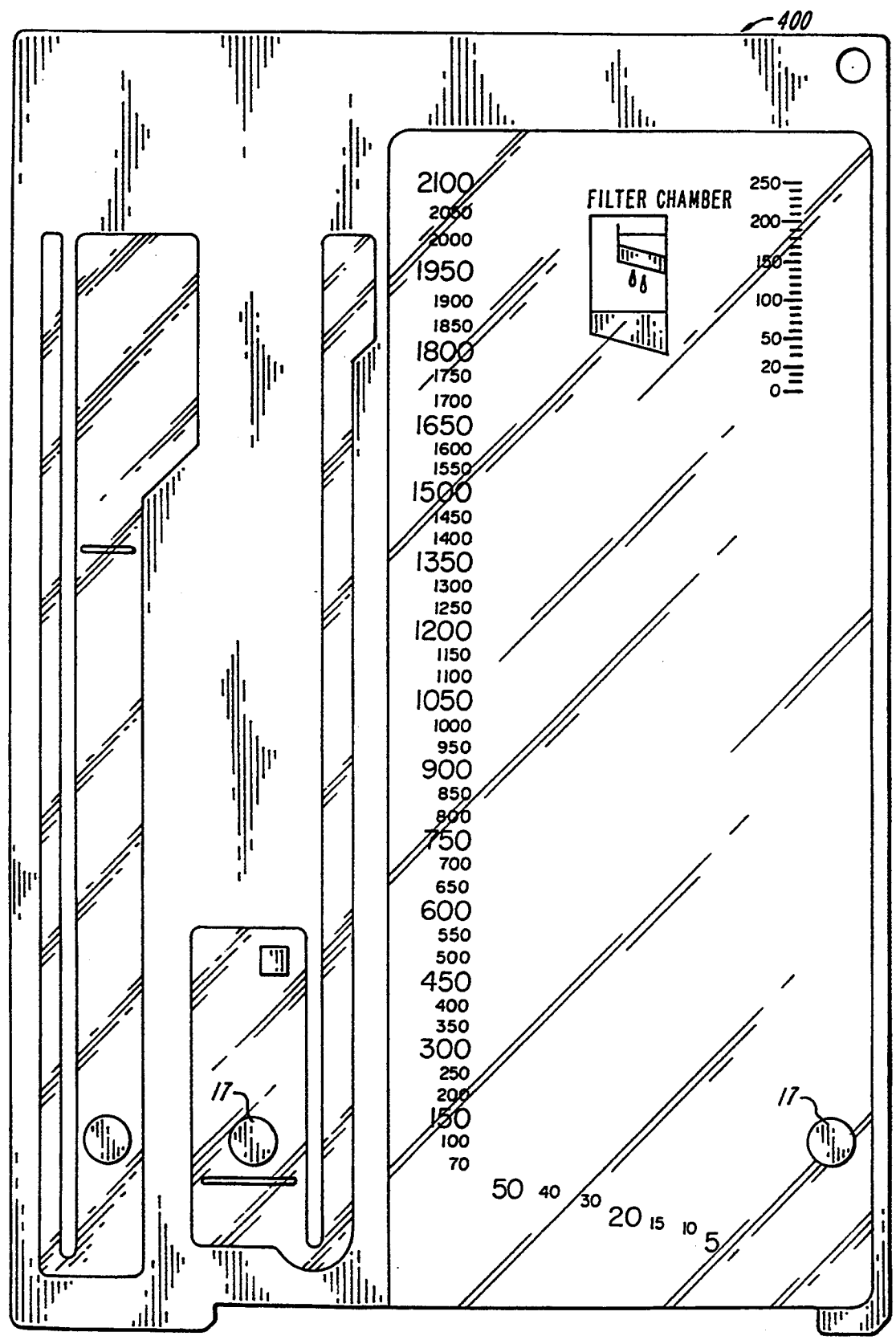

FIG. 9B shows a front panel template for such an undivided embodiment. As shown, the display has uniform and highly visible graduations with a scale providing an effective resolution of about fifty milliliters over a range from (0.1) to (2.1) liters. The slanted floor 341 (FIG. 1) provides a somewhat expanded scale for the first seventy milliliters, although low end accuracy of this embodiment is limited by the plumpness of the drain in addition to meniscus effects.

When it is intended to use the collected fluids for reinfusion, an outlet structure is attached to reinfusion/outlet port 19. Port 19 is located at the lowest point of the drain, and has a large bore infusion tube attached thereto, with a pinch clamp. At the end of the tube, an IV spike port having a diaphragm seal and reclosable cap are preferably attached to allow sterile connection to a transfer vessel or to an infusion pump or line. The position of port 19 and the slopes of walls 341, and 338, 339 assure that full volume of collected blood is drawn out, thus minimizing the risk of contaminating subsequently collected fluid. The large bore IV tubing allows fast delivery of the collected fluid.

Preferably, the internal wall structure at the collection chamber side of the drain is configured substantially as illustrated in FIG. 1, but with walls 339, 338 and 337 forming a fully continuous barrier between chambers 12c and 12d, so that all drainage goes to chamber 12c until accumulation of the 750 cc overflow volume. Each collection chamber has a floor 338, 341 that slopes at a small angle, between about 5 and 30 degrees, so that the fluid rising over the floor extends several times more quickly in a horizontal direction than it rises vertically. By laying out the volume readings along this slope, applicant provides a fine resolution of collected fluid volume during the stage of collection prior to the floor being entirely submerged.

As in the previously described embodiment, the thin throat between the outside wall and wall 339 is dimensioned to quickly fill with approximately 100 ml. volume, being formed with a relatively shallow rear wall to achieve such volume capacity over a relatively long, e.g., 10–15 cm rise. Thereafter the middle wall portion 338 constituting the floor of the upper chamber 12 c is angled to resolve another 100 ml. in collected fluid once the neck has filled. Thus, the first 200 ml of blood falling through the filter into the primary chamber 12c are displayed with a resolution of 5–10 ml./cm, the volume and resolution scale thus being suitable for collecting and monitoring pediatric bleeding, or for displaying reinfusion volumes in either a pediatric or adult setting.

As collected blood volume rises, the first chamber 12c continues to display the fluid level up to its overflow volume of 7–800 ml, with the display scale advantageously positioned midway up the face of the device. As noted above, the neck and floor graduations of chamber 12c provide high resolution of the first 200 ml. of fluid, after which the graduation scale factor is diminished.

When collected fluid exceeds 750 ml and overflows, the sloped floor 341 of the overflow chamber 12d provides a several-fold run-to-rise ratio that again provides a high resolution of the collected fluid volume, and allows a quick assessment of the rate of bleeding once blood loss has attained the 750 ml level of significance. Once the floor 341 is entirely covered, the fluid level rises more slowly to the maximum container volume of slightly over two liters.

Figure 1A:
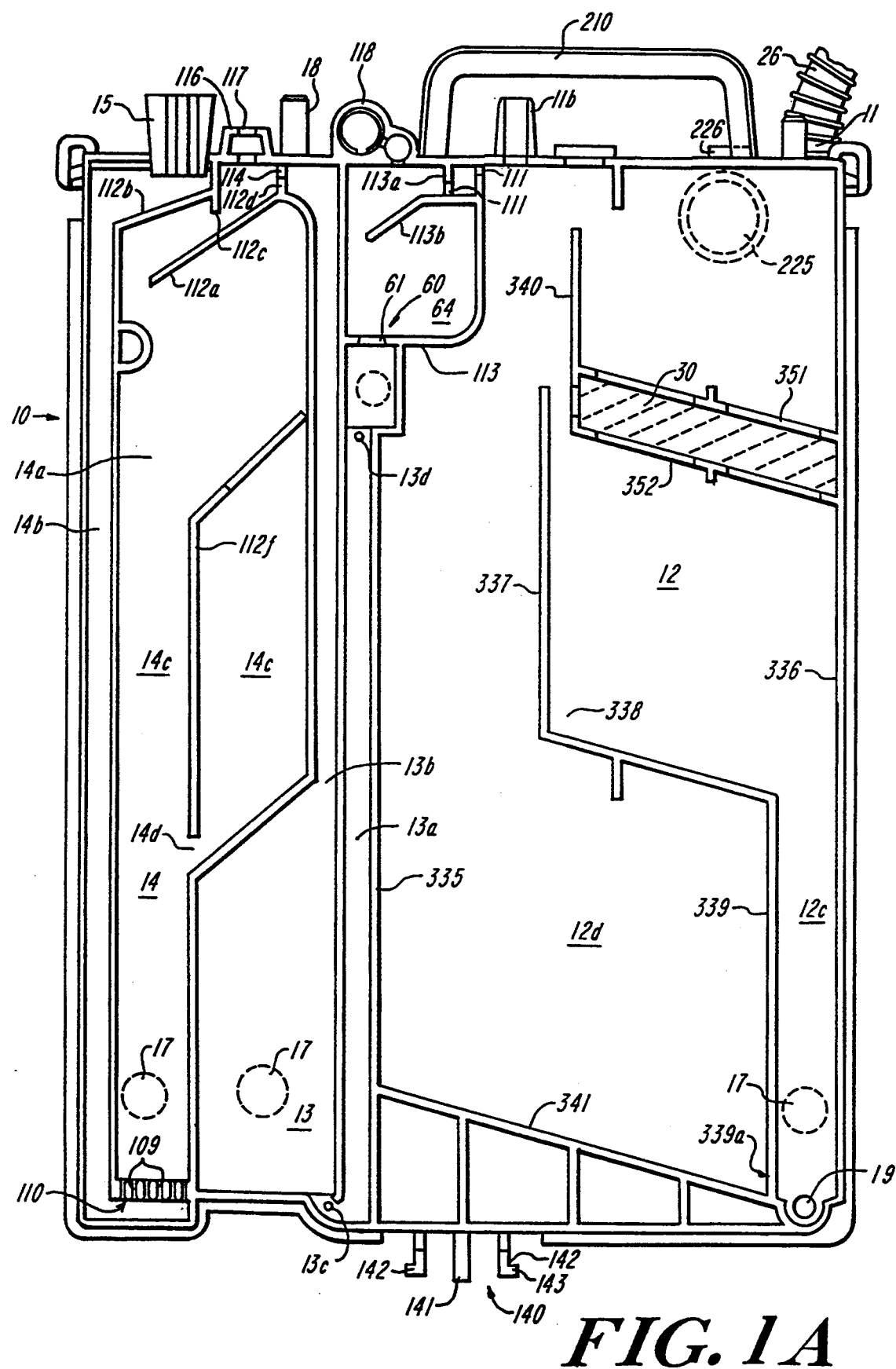
FIG. 1A is a front elevation of another embodiment having many characteristics similar to that of FIG. 1.

Preferably this drain is configured as illustrated in FIG. 1A, with two patient drain tube inlets 11, 11b positioned respectively over the filter 30 and the large volume chamber 12d. This "split" drain construction allows one to operate the drain as a pediatric drain or an autotransfusion drain for collecting filtered blood, by simply attaching the right hand tube, at inlet 11, to the patient or collection wand. Similarly, if it is only desired to collect massive flows of blood during surgery, the center tube at inlet 11b may be attached to the patient or wand, filling chamber 12d.

Figure 9C:
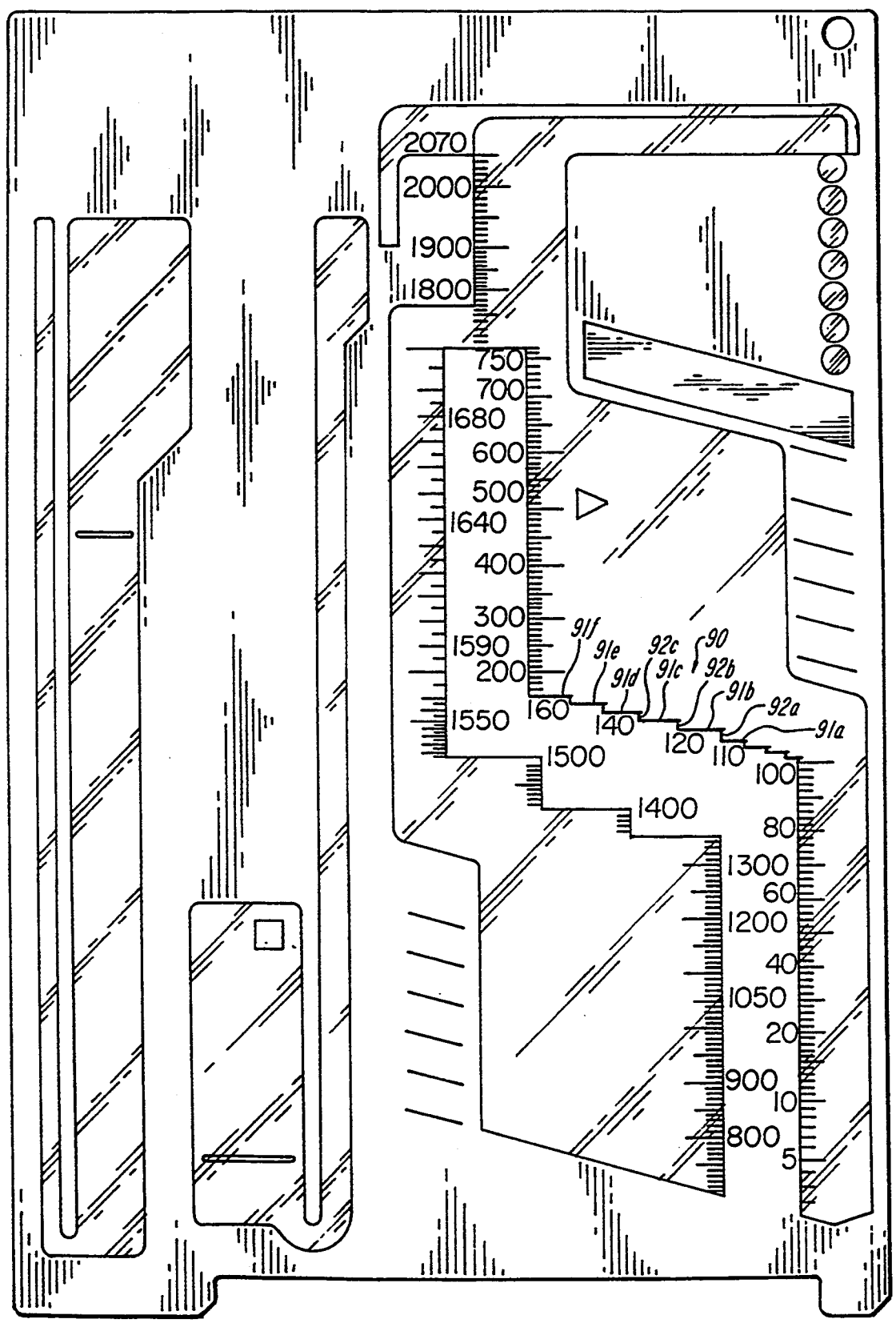
FIGS. 9C, 9D and 9E show graduation decals for enhanced perception of fluid volume, and an enlarged detail.

Preferably, a face plate decal identifies the contents of each chamber, as indicated in the legends "COLLECTION ONLY" or "ATS CHAMBER" shown in FIG. 9C. This face plate decal also includes the volumetric graduations described above.

Applicant has found that the volume display as fluid climbs the sloping floor regions defined by walls 338, 341 poses some perceptual problems owing to the shallow angle at which the horizontal fluid surface intersects the floor. Applicant has found that the true volume is more readily ascertained by providing step-like graduation graphics on the front panel such that the fluid surface level defines an abrupt corner, intersecting the graphics at a steep angle, rather than the shallow angle characteristic of conventional horizontal graduation lines.

Figure 9D:
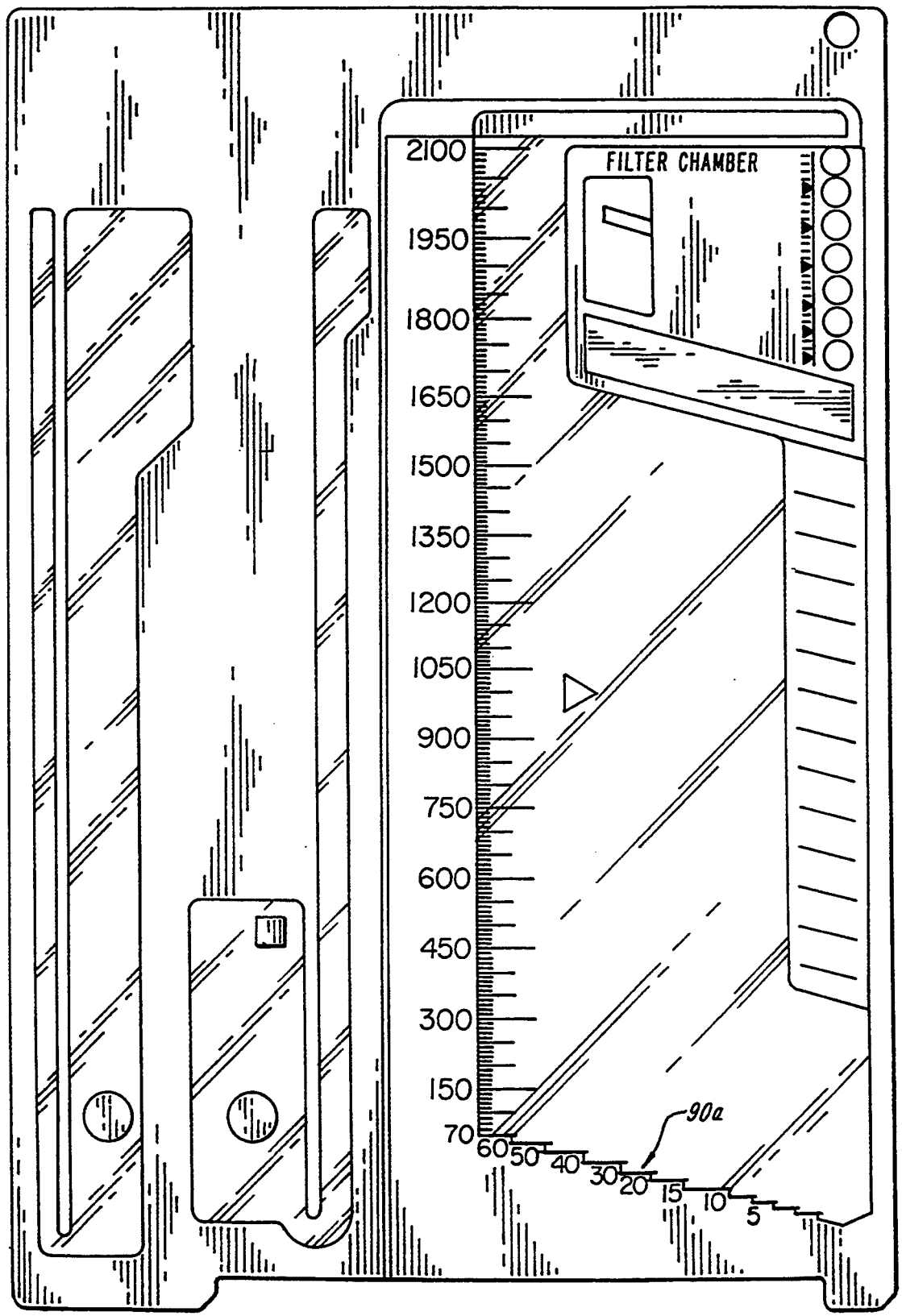
Figure 9E:
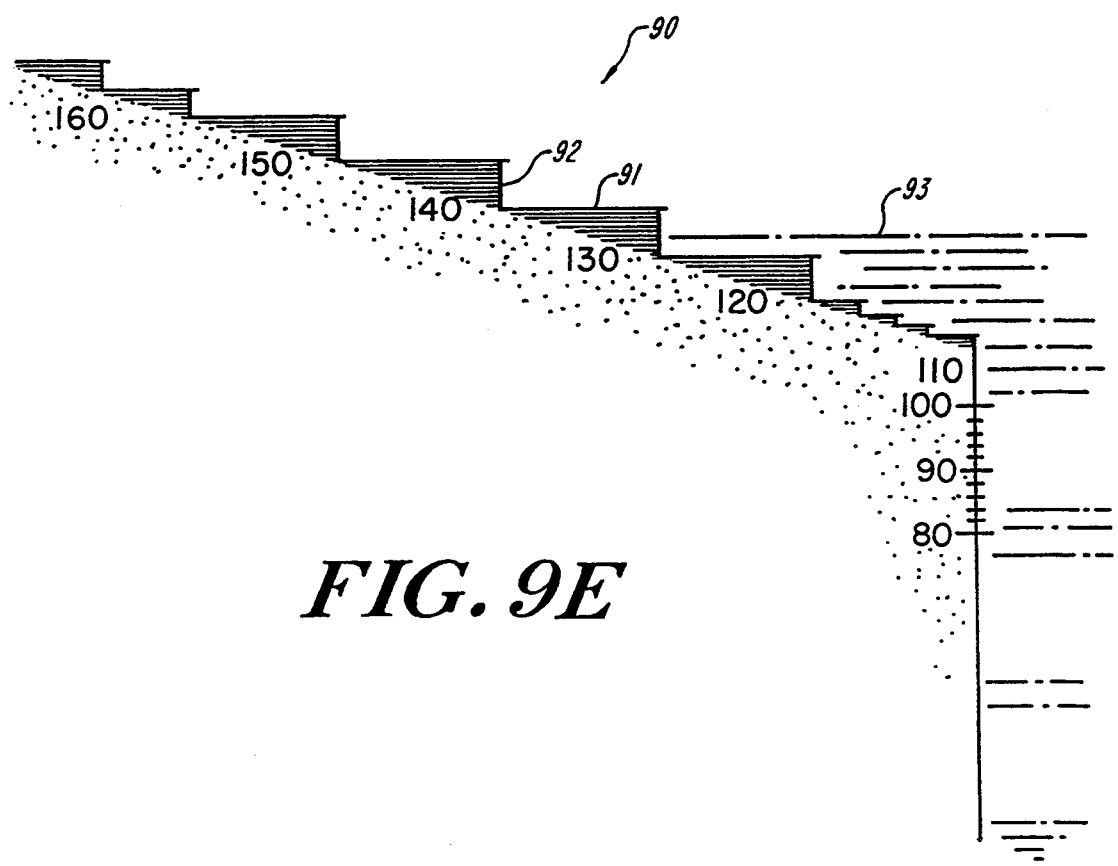

FIG. 9C shows such a front graphics panel. A staircase decal 90 has a solid block graphic staircase that follows the fluid level up the shallow slope, so that as the fluid level rises above a stair flat 91a it forms a clearly visible corner with the riser 92a leading to the next stair. An enlarged detail view illustrating the fluid level 93 intersecting the staircase graphics 90 is shown in FIG. 9E. The staircase pattern of repeated flats and risers makes the precise fluid level clearly visible as a discontinuity in the next flat 91b. This type of discontinuity feature can be distinguished from any angle, even, for example, when the drain is located at floor level across a room, and observed along a relatively steep downward or cross-ways view line. FIG. 9D shows a corresponding front graphics template having a jagged graduation scale 90a for resolving fluid volume at the bottom of the large chamber 12d. This volume scale corresponds to the template of FIG. 9B, i.e., shows the volume readings for a single large chamber, rather than split-chamber device. The staircase graphics of FIGS. 9C or 9D may be replaced by a plurality of thin graduation lines extending horizontally across the face at spacings corresponding to five or ten cc increments. Such graduation lines are preferably of a bright white or similarly contrasting color.

Preferably, however, as noted above, the drain device according to the present invention is implemented as a single device having multiple drainage capabilities due to the vertical and horizontal offsets of internal chambers 12c, 12d.

Specifically, the device functions as pediatric measuring drain or reinfusion system, as a graduated collection/reinfusion vessel for relatively slow wound drainage, or as a collection/reinfusion vessel for the relatively massive levels of bleeding associated with open chest surgery. Furthermore, when an additional patient inlet tube is located over the neck of chamber 12d, the device may function as a two-site collection vessel, with the collected fluid volume from each site separately displayed while the fluid from only one site is filtered for re-use. A single drain unit thus fulfills the functions of three or more slightly differing drain units of the prior art, characteristically found in the hospital wards, pediatric units, thoracic operating rooms and ICU's. This multiple-use capacity greatly simplifies and reduces the cost of hospital inventory requirements and provides a uniform system of set up for all units, so that personnel from all wards can set up the unit for any purpose.

The provision of an ATS chamber 12c having its principal volumetric scales located midway up the face place enhances the visibility of fluid level when the device is hung from a bed or stood on the floor, while the provision of a large cardiotomy-type chamber 12d using the full-face graduations provides good visibility at the working level when the drain is used in a surgical setting. The slanted floors and long neck of chamber 12c further assure that all collected blood in that chamber can be reinfused through exit port 19 without breaking the seal formed by the pooled blood, and without introducing air into the infusion line.

FIG. 10 shows a back view of the molded body portion 105 of the two-piece housing of drain 10a. The rear wall portion 105 consists of an arrangement of substantially rectangular panels each of which is vertical, horizontal or sloping front-to-back or side-to-side, and defines all or a portion of a side or rear wall of one or more of the sub-chambers or water columns described above in respect of FIG. 1 or 1A. In this preferred embodiment, each of the substantially rectangular back panels lies parallel to the front panel at a depth "d" which is one of a few discrete values. In the illustrated prototype embodiment, which has an overall thickness or chamber depth of approximately two inches, the depth values A, B, C, E or F are given in the following table.

TABLE II

| Depth "d" | Inches |
|---|---|
| A | ¼ |
| B | ½ |
| C | 1 |
| E | 1¾ |
| F | 2 |

The regions marked "S" in FIG. 10 are each uniformly slanted back or side wall portions which lead from one chamber depth or width to a different chamber depth or width.

This block-body structure has been found to provide particularly advantageous pressure response characteristics for the columns and chambers defined thereby, when used in conjunction with the various limiting valves or pressure modulation structures described above. Of particular note in this regard, applicant notes that the downstream column of the water seal includes the cube-like deep box marked in FIG. 10, which serves as the sealing pool. This deep broad box does not spill its contents when the drain is tipped onto its back, since the top portion of that column, at the shallow depth A from the face plate, is approximately 1½ inches above the back, at roughly twice the height of the water seal pool. Also of note is the broad uniform taper of the downstream column of the manometer chamber, including the collateral fluid return chamber 14c which promotes side circulation of fluid as described above.

Figure 10A:
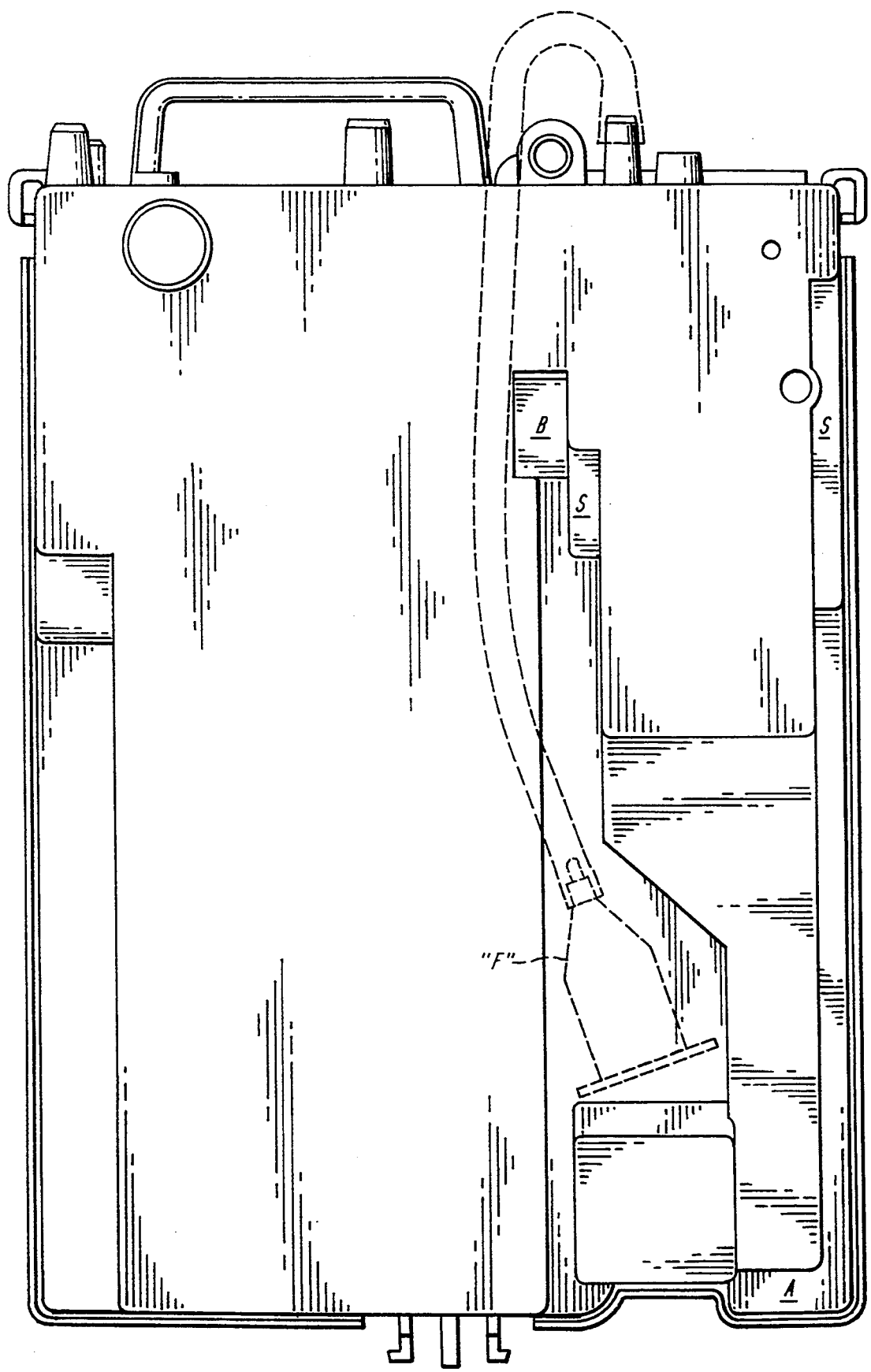
FIG. 10A is a back view of the same drain device receiving an accessory fitted therein.

In a preferred embodiment, the recesses in the back surface created by the juxtaposed box walls and slant faces serve as protective recesses for receiving auxiliary fittings that are pre-attached to hoses extending from one or more of the drain ports, thus protecting these fittings during shipment while simplifying unpacking and initial set up of the drain. FIG. 10A illustrates such a pre-set up unit, with a filler funnel "F", illustrated in phantom, positioned in the recess determined by the shape of the downstream column of the manometer chamber.

Figure 12:
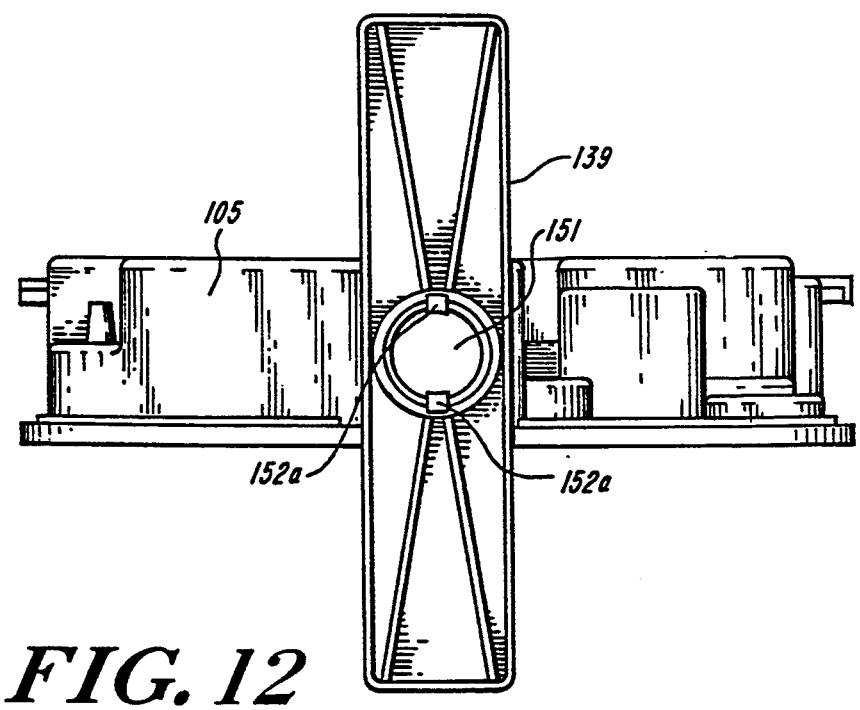
FIG. 12 is a bottom view of the drain device, with a different pedestal mounting structure.

FIGS. 11-14 show additional external views of the presently preferred embodiment of a drainage device, illustrating in detail the contours and locations of the various wall, port, support and other features formed in the molded housing in this preferred construction. Among other details, these drawings show clearly the relatively large patient inlet port 11 which connects to and is preferably pre-packaged with, a large-diameter flexible latex thoracotomy tube. The transfer/infusion port 19a by contrast, connects to a smaller blood-compatible PVC or similar tube. Preferably, the drain device is pre-packaged with a short, e.g., half-meter length of such tubing mounted on the port 19a, and having a sealed diaphragm-type spike port at its end. FIG. 12 shows another variant of the pedestal mounting structure, wherein a cylindrical shaft 151 with stops 152a is formed on the housing 105. Pedestal 139 is rotatably secured on shaft 151 by the stops, which also serve as detents to lock the pedestal perpendicular to the plane of the device when the pedestal is rotated.

Figure 13A:
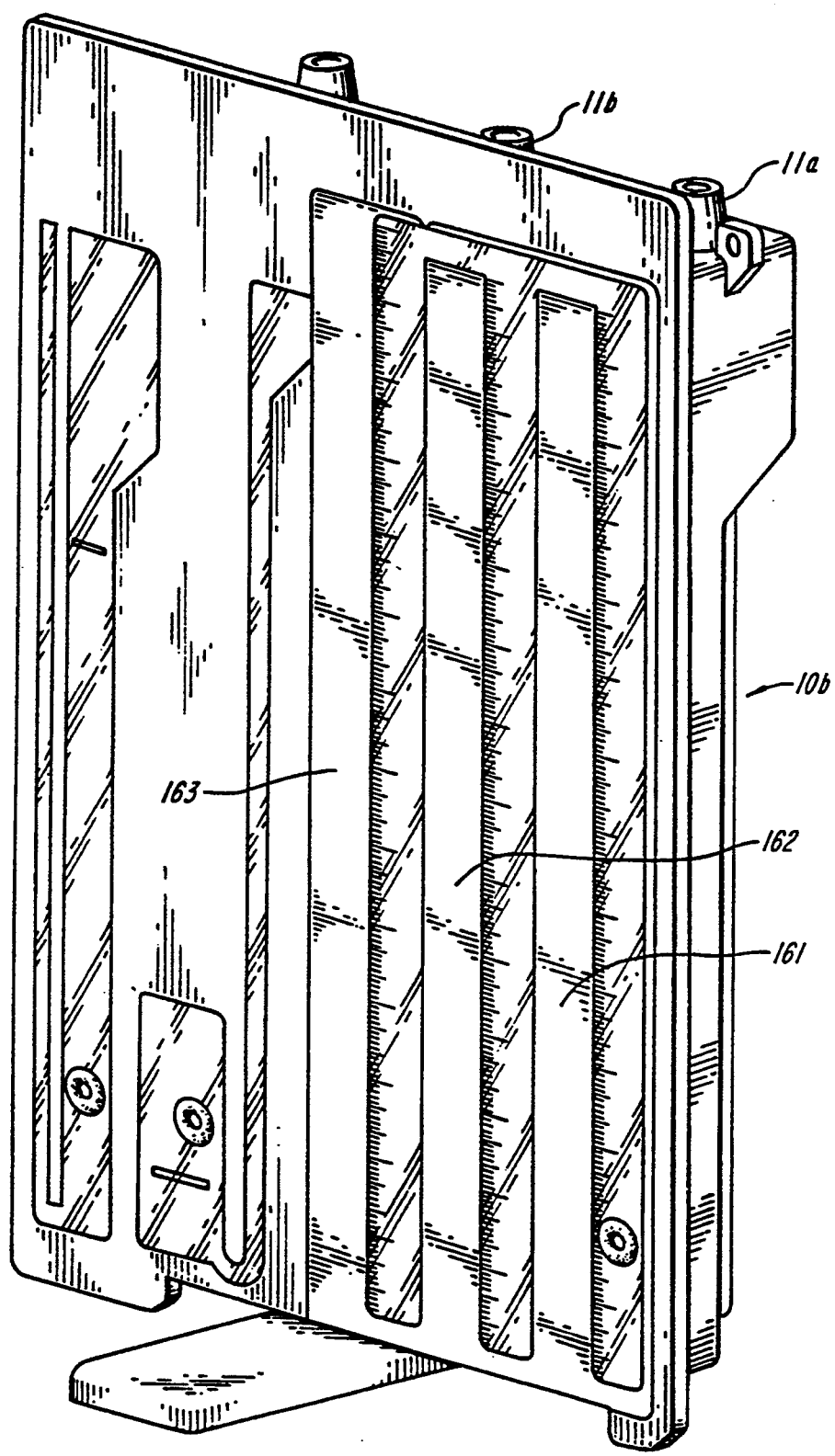
FIGS. 13A, 13B and 14 are front perspective views of three different drain devices embodying aspects of the invention.
Figure 13B:
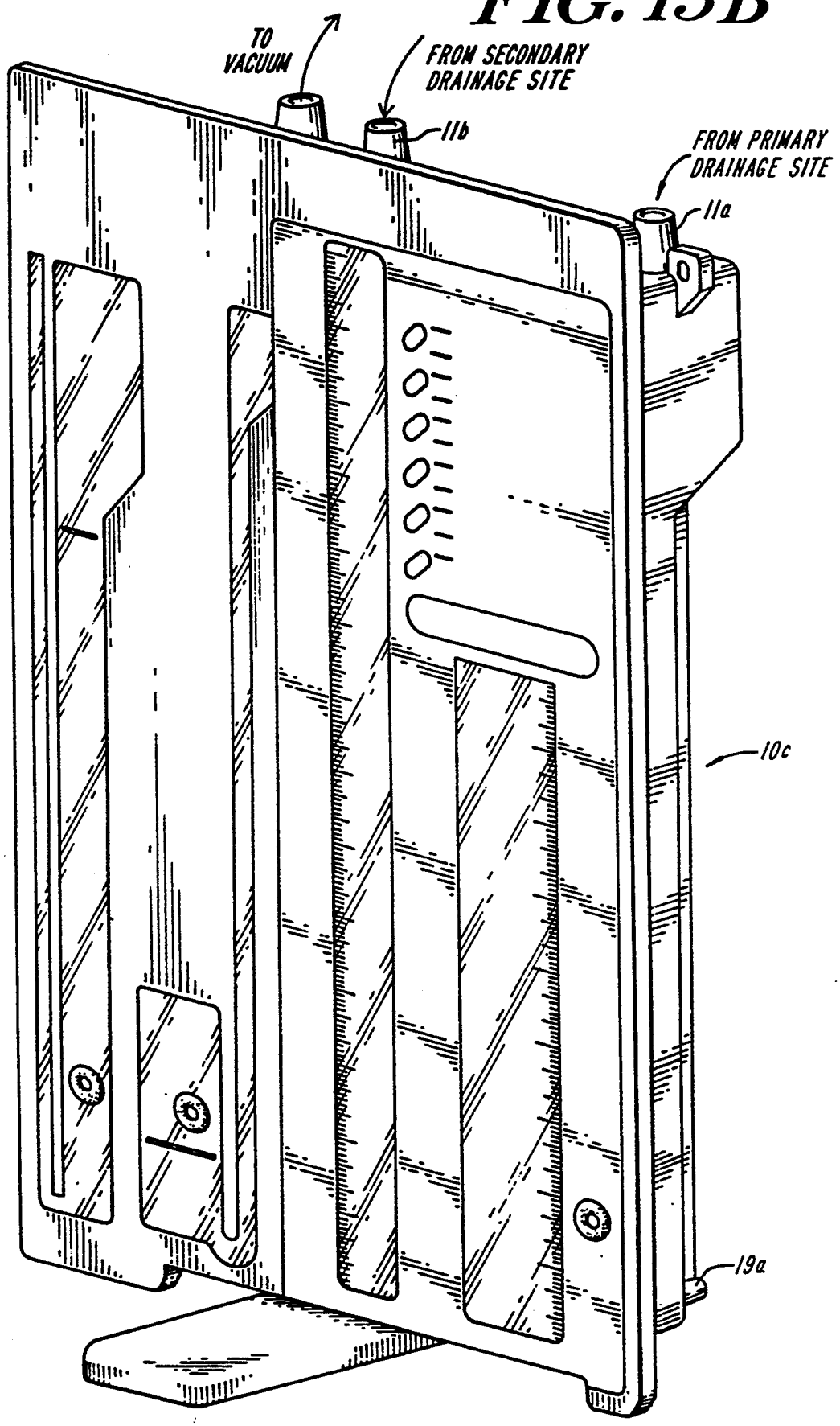
Figure 14:
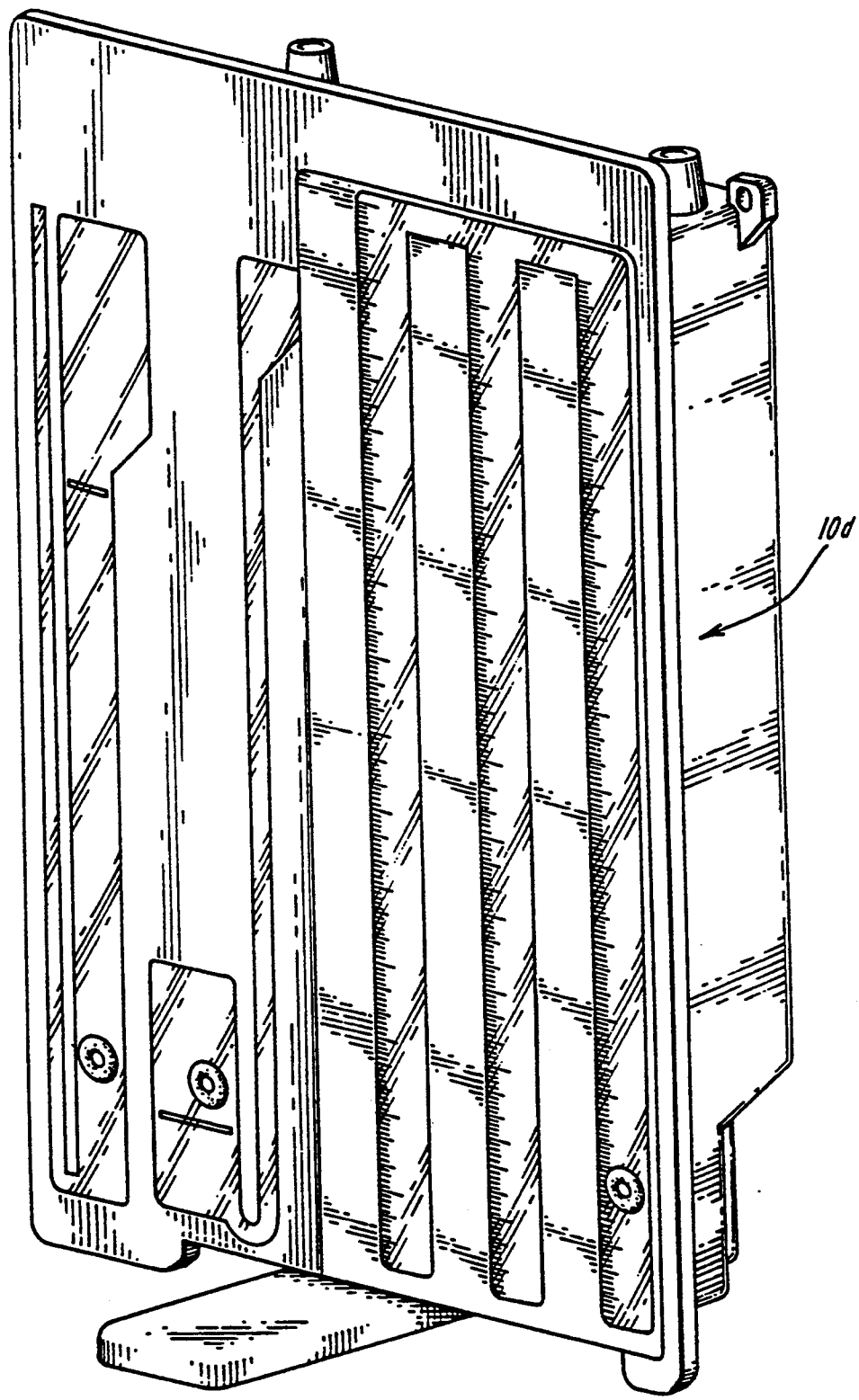

One or more of the foregoing features of the drain device are also advantageously incorporated into different drain devices illustrated in FIGS. 13-14.

FIG. 13A shows another drain device 10b which is specially adapted to collect fluids from several sites via plural patient fluid inlet ports 11a, 11b. In this device, the manometer and water seal chamber structure are substantially identical to those illustrated in the previous Figures, but the inlet ports 11a, 11b lead to different collection chambers so that the volume of fluid collected from each site may be separately ascertained from the graduated windows 161, 162, 163. In this embodiment no outlet port or gross filter is provided, and the drain serves to collect fluid and monitor collected fluid levels. It is thus not intended for fluid reinfusion. A principal collection chamber under inlet 11a has two columns located behind windows 161 and 162, respectively. A continuous wall similar to wall 337 of FIG. 5, but extending vertically straight to the bottom, separates the two columns and assures that first one column fills and then overflows to fill the other column. Behind window 163 a single isolated secondary collection column receives fluids only from inlet 11b, and separately indicates their volume.

FIG. 13B shows another drain embodiment 10c having two patient inlets 11b, 11a. In this embodiment, a filter and an outlet port 19a are provided for prefiltering and reinfusion of the fluid collected via inlet 11a, which is the primary inlet for mediastinal fluid drainage. Secondary inlet 11b provides unfiltered collection from a secondary site, such as one at the apex of the lung, into a preferably isolated separate graduated column.

FIG. 14 shows another drain unit 10d with a single inlet and no outlet. In this embodiment, first and second inner walls preferably define successive overflow paths to fill first one column, then the second, then the third. Again no gross filter or fluid outlet is provided. The volumes of various collection chambers may be readily altered by forming the internal walls at different locations. One desirable variant is to form a pediatric drain, utilizing the same water column structure as the preceding devices. It preferably includes neither a gross filter nor an outlet port. The inner walls corresponding to walls 337, 338, 339 of FIG. 1 are modified to define a single collection column located behind a volume display window and the column is dimensioned such that its full height corresponds to a fluid volume of only approximately two to five hundred cubic centimeters. A broad portion of the graphics panel covering the dead space between the collection column and the water seal preferably has a bright engaging picture thereon to psychologically enhance the hospital room environment.

Thus, the drain device according to the present invention is adapted, with minor changes of straight interior wall portions and different printing on the front face, to provide a stable and sterile suction drainage device for a variety of drain applications and autologous blood circuits.

It will be appreciated that different ones of the novel features shown can be used independently of others and in a variety of drain device forms and structures. It will thus be seen that a chest drain device according to the invention efficiently attains the objects set forth above as well as those made apparent from the preceding description. Since changes may be made in the illustrated device without departing from the scope of the invention, all matter contained in the above description or shown in the accompanying drawings is to be interpreted as illustrative and not in a limiting sense.

Having described the invention, what is claimed as new and secured by letters patent is:

1. An improved vessel for collection of body fluids, such vessel comprising a molded body having outer walls and an open side, plural internal dividers, a face plate which closes said open side whereby the dividers separate the molded body into plural distinct subchambers, and wherein the molded body includes a passageway passing through one of said outer walls between interior and exterior of the vessel, and a valve element in said passageway for regulating pressure in the subchambers, said passageway also having an opening at the plane of the fact plate such that assembly of the face plate onto the molded body secures the valve element in position.

2. A vessel according to claim 1, wherein the passageway passes through an upper surface of the molded body, and contains a filter to filter air passed by the valve element.

3. A vessel according to claim 2, wherein the passageway includes a chamber and the valve element includes a member mounted for movement in the chamber between open and closed positions, and means for biasing the member in a closed position.

4. A vessel according to claim 1, wherein the molded body includes two separate passageways located above separate subchambers, each passageway having an opening which is closed by the face plate to secure a valve therein.

5. A vessel according to claim 4, wherein the two separate passageways accommodate positive and negative pressure release valves, respectively.

6. A vessel according to claim 5, wherein one said passageway includes an aperture and a centering structure adapted to align a check ball with the aperture.

7. A vessel according to claim 1, wherein the passageway includes a recess extending from a position coplanar with the face plate into the molded body portion for receiving a filter element to filter air as it passes the valve element.

8. A vessel according to claim 1, wherein the valve element is a check valve and the passageway includes a barrier wall having an aperture that is selectively closed by the check valve.

9. A vessel according to claim 4, wherein one said passageway further includes a filter.

10. A vessel according to claim 1, wherein said passageway includes an aperture and a centering structure for aligning a check ball with the aperture.

11. A vessel according to claim 1, wherein the passageway includes a surface opening defining a flexible finger in the surface of the body, the flexible finger constituting a manually-operable release for moving said valve element.

12. A vessel according to claim 4, wherein one said passageway contains a manually-actuated valve and the other said passageway contains a self-operating valve.

13. A vessel according to claim 1, further comprising a suction port in said body portion, and a large bore stopcock connected to said suction port for regulating draw therethrough.

14. A vessel for collecting body fluid, such vessel comprising a first part constituting a body having outer walls, internal divisions and an open face, and a second part in the form of a face plate which is assembled to the first part to close the open face forming a vessel such that the internal divisions separate the vessel into subchambers, wherein the body includes passage means extending through an outer wall adjacent the open face and having an opening at the plane of the face plate, and further comprising valve means secured in said passage means by the face plate when it is affixed over the open face.

15. A vessel according to claim 14, wherein said passage means opens outwardly through a wall of said body opposite the face plate.

16. A vessel according to claim 14, wherein said passage means opens outwardly through a wall of said body adjacent the face plate.

17. A drain for aspirating biological fluid from a patient, such drain comprising a body having a back interior surface and plural dividers extending from the back interior surface to channel fluid communication within the body, a face plate sealingly affixed to the body along outer edges thereof such that at least some of the dividers contact the face plate to define separate intercommunicating subchambers of a multichamber collection vessel formed by said body and face plate, wherein one subchamber extends laterally from one side of the vessel and is positioned below an inlet to form a collection chamber for receiving body fluids drawn to said inlet by suction applied to said one subchamber, the body including a knockout formed adjacent an upper side portion of said subchamber that breaks away to form an opening for decanting collected fluid.

18. The drain of claim 17, wherein the body further includes a boss extending outwardly therefrom at a position proximate to the knockout as a leverage point for manually pressing out the knockout.

19. The drain of claim 18, wherein the knockout is substantially circumscribed by a thinned annular region such that a central portion thereof breaks off to fall within said subchamber when pressed.

20. The drain of claim 17, wherein the body includes passage means integrally molded with said body for providing air communication through a wall thereof, and valve means located in said passage means for regulating air communication through the passage means, and wherein the face plate seals the valve means in the passage means.

21. A drain vessel for collection of body fluids from a patient by aspiration, such vessel comprising plural walls defining a multichamber container wherein intercommunicating subchambers define a series of enclosed volumes for constituting a fluid collection chamber and for regulating suction in the collection chamber while sealing the chamber from contamination by the surrounding atmosphere, such drain vessel including means for holding the vessel in a vertical orientation such that body fluids enter the vessel through a collection tube attached at the top of the vessel and flow downwardly to pool in the collection chamber, and further comprising an opening positioned in a substantially horizontally extending wall of the vessel above the collection chamber and a horizontally disposed pierceable injection port extending as a horizontal surface across the opening and sealing the opening, whereby liquids are conveniently injected into the collected fluid without destabilizing the vessel.

22. A drain vessel according to claim 21, further comprising filter means located between the collection tube and a pooling region in the collection chamber, and wherein the injection port is located over the filter means for applying material thereto.

23. A drain vessel according to claim 22, wherein the filter means has an inclined surface for directing clots to a lower edge of the filter.

24. A drain vessel according to claim 21, wherein the means for holding the vessel in a vertical orientation includes at least one of a pedestal mechanism or a hanger mechanism.

25. A drain vessel according to claim 21, wherein the vessel is assembled from a first portion comprising a molded body with a back wall and surrounding edge walls, and a second portion comprising a face plate that attaches to the surrounding edge walls to form a front wall that closes the vessel.

26. A drain vessel according to claim 25, wherein the molded body includes a handle protruding from the body and integrally molded therewith.

27. A drain vessel according to claim 26, wherein the face plate extends above the molded body to shield the handle from snagging.

28. A drain vessel according to claim 21, wherein the collection chamber is located off-center in said drain vessel, and further comprising a handle protruding from said molded body and substantially centered over the collection chamber.

29. A drain vessel according to claim 21, further comprising a handle located off-center on a side of said vessel at a balance point thereof.

30. A drain vessel for the collection of body fluids from a patient by aspiration, such vessel comprising plural walls closed by a front face plate and defining a multichamber container wherein intercommunicating subchambers define a series of enclosed volumes for constituting a fluid collection chamber and for regulating suction in the collection chamber while sealing the chamber from contamination by the surrounding atmosphere, such drain vessel including means for holding the vessel in a vertical orientation such that body fluids enter the vessel through a collection tube attached at the top of the vessel and flow downwardly to pool in the collection chamber, wherein the fluid collection chamber is located off-center at one side of the drain vessel, and further including a U-shaped handle extending upward from a top horizontal surface behind the face plate of the multi-chamber container and substantially centered over the fluid collection chamber.

31. A drain vessel according to claim 30, wherein the handle is integrally molded with said vessel.

32. A drain vessel according to claim 31, wherein said vessel comprises a generally open-faced box, at least one ribbon divider extending thereacross, and the face plate closing the box, said handle being molded with the open-faced box.

33. A drain vessel according to claim 32, wherein the face plate extends vertically above the open-faced box and shields the handle from catching on dangling objects.

34. A drain vessel for the collection of body fluid, such vessel comprising
a receptacle, including therein
first means for establishing a selected level of suction in said receptacle when attached to an unregulated suction source
a collection chamber
second means for establishing a water seal barrier between the first means and the collection chamber to isolate the collection chamber from backflow of air
inlet means for admitting fluid to the collection chamber, and
injection port means above the collection chamber for injecting material into fluid admitted by the inlet means, said injection port means including an opening located in a horizontal surface of said receptacle and including a pierceable element extending as a horizontal surface across the opening parallel to said surface of said receptacle whereby injections are conveniently made using one hand without tipping the drain vessel.

35. A drain vessel for collection of body fluid, such vessel comprising
a receptacle, including therein
first means for establishing a selected level of suction in said receptacle when attached to an unregulated suction source
a collection chamber
second means for establishing a water seal barrier between the first means and the collection chamber to isolate the collection chamber from backflow of air
an inlet located over the collection chamber,
a U-shaped handle extending acentrically upward from a top surface of the receptacle and centered over said collection chamber, and
shield means for preventing the handle from snaring.

36. A drain vessel for the collection of body fluid, such drain vessel comprising an open body including outer walls, plural internal dividing walls, a face plate closing the open body thereby defining a closed vessel with plural distinct subchambers interconnected via openings in the dividing walls, and a rotational support structure formed in a bottom wall of said open body, wherein the rotational support structure includes first means for pivotally joining said body and a pedestal member for rotation about a pivot axis and second means for providing a rotatable snap-connection of said body and the pedestal member, said second means limiting deflection from said pivot axis such that when mechanical forces cause breakage of said second means said first means remains intact for maintaining the body upright.

37. A vessel according to claim 36, wherein the first means includes at least one of a centering pin or a bushing.

38. A vessel according to claim 37, wherein the second means includes a plurality of spring claws that engage the pedestal member about an arcuate surface.

39. An improved vessel for collecting body fluids, such vessel comprising a molded body having outer walls and an open side, a face plate extending in a plane for covering said open side to form a closed receptacle, means for applying a defined level of suction to the closed receptacle and means for admitting body fluids drawn by the suction to said closed receptacle, wherein the molded body includes a valve chamber communicating through a wall of the molded body with an interior volume of said closed receptacle, said valve chamber having a first opening at the plane of the face plate and coplanar with said open side so that it is covered by the face plate, and a second opening communicating with surrounding air, and further includes, a valve body located in said valve subchamber for effecting valved communication between the interior and the second opening, said valve body being confined in said valve chamber by positioning the face plate over said first opening.

40. An improved vessel according to claim 39, wherein the valve chamber is integrally molded with said molded body.

41. An improved vessel according to claim 40, wherein said second opening circumscribes a manually operable release button for moving said valve body.

42. An improved vessel according to claim 41, wherein the release button is integrally molded with said housing.

43. An improved vessel according to claim 1, wherein the vessel includes a chamber for collecting fluid, said chamber having a wall that is angled for increasing run-to-rise of a collected fluid contacting the wall, and further includes a window in the face plate in registry with said angled wall for displaying collected fluid volume.

44. An improved vessel according to claim 43, wherein the wall that is angled is a filter element defining a floor of a filter chamber.

45. An improved vessel according to claim 43, wherein the wall that is angled is a portion of a floor of a collection chamber that is angled to funnel collected fluid to an outlet for reinfusion.

* * * * *

UNITED STATES PATENT AND TRADEMARK OFFICE
CERTIFICATE OF CORRECTION

PATENT NO. : 5,397,299
DATED : March 14, 1995
INVENTOR(S) : Theodore Karwoski, Steve A. Herweck, and David Cross It is certified that error appears in the above-indentified patent and that said Letters Patent is hereby corrected as shown below:

On title page item [75], replace "Karwiski" with --Karwoski--.

Column 27, line 15, replace "fact" with --face--.

Signed and Sealed this

Nineteenth Day of May, 1998

Attest:

BRUCE LEHMAN

Attesting Officer                Commissioner of Patents and Trademarks